(12) United States Patent
Shaked et al.

(10) Patent No.: US 11,998,331 B2
(45) Date of Patent: Jun. 4, 2024

(54) USE OF MICRO-RIBONUCLEIC ACID (miRNA) TO DIAGNOSE TRANSPLANT REJECTION AND TOLERANCE OF IMMUNOSUPPRESSION THERAPY

(71) Applicant: THE TRUSTEES OF THE UNIVERSITY OF PENNSYLVANIA, Philadelphia, PA (US)

(72) Inventors: Abraham Shaked, Wynnewood, PA (US); Bao-Li Chang, Paoli, PA (US); Brendan Keating, Philadelphia, PA (US); Toumy Guettouche, Miami, FL (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 16/365,194

(22) Filed: Mar. 26, 2019

(65) Prior Publication Data

US 2019/0313957 A1 Oct. 17, 2019

Related U.S. Application Data

(63) Continuation of application No. 15/302,815, filed as application No. PCT/US2015/025382 on Apr. 10, 2015, now abandoned.

(60) Provisional application No. 61/977,980, filed on Apr. 10, 2014.

(51) Int. Cl.
| | | |
|---|---|---|
| *C12Q 1/6883* | (2018.01) | |
| *A61B 5/15* | (2006.01) | |
| *A61B 10/00* | (2006.01) | |
| *C12N 15/113* | (2010.01) | |
| *G16B 25/00* | (2019.01) | |
| *G16B 25/10* | (2019.01) | |
| *G16B 25/20* | (2019.01) | |
| *G16H 50/50* | (2018.01) | |

(52) U.S. Cl.
CPC ............ *A61B 5/15* (2013.01); *A61B 10/0038* (2013.01); *A61B 10/007* (2013.01); *C12N 15/113* (2013.01); *C12Q 1/6883* (2013.01); *G16B 25/00* (2019.02); *G16B 25/10* (2019.02); *G16B 25/20* (2019.02); *G16H 50/50* (2018.01); *A61B 2010/0061* (2013.01); *C12Q 2600/158* (2013.01); *C12Q 2600/178* (2013.01)

(58) Field of Classification Search
CPC .............................................. C12Q 2600/178
See application file for complete search history.

(56) References Cited

U.S. PATENT DOCUMENTS

| | | | |
|---|---|---|---|
| 9,790,552 B2 | 10/2017 | Feinberg | |
| 2002/0155117 A1* | 10/2002 | Suciu-Foca | ...... C07K 14/70539 |
| | | | 424/185.1 |
| 2006/0099619 A1 | 5/2006 | Remacle et al. | |
| 2012/0101001 A1 | 4/2012 | Suthanthiran et al. | |
| 2012/0295810 A1 | 11/2012 | Quake et al. | |
| 2014/0017218 A1 | 1/2014 | Scott et al. | |
| 2014/0256562 A1* | 9/2014 | Umansky | ................ A61P 25/28 |
| | | | 506/2 |
| 2017/0130267 A1* | 5/2017 | Duong Van Huyen | ..................... |
| | | | C12Q 1/6883 |

FOREIGN PATENT DOCUMENTS

| | | |
|---|---|---|
| WO | 2005111211 A2 | 11/2005 |
| WO | 2008079303 A2 | 7/2008 |
| WO | 2010105275 A2 | 9/2010 |
| WO | 2013036282 A2 | 3/2013 |

OTHER PUBLICATIONS

Liang et al (BMC Genomics 2007, 8:166, 20 pages) (Year: 2007).*
Weber et al (Clinical Chemistry 56:11 1733-1741 (2010)) (Year: 2010).*
Volpin et al (Liver Transplantation 8(6):527-534, 2002) (Year: 2002).*
Applied Biosystems, TaqMan Human MicroRNA Arrays Product Sheet, Jun. 2008.
International Search Report and Written Opinion dated Oct. 7, 2015—PCT/US2015/025382.
Supplementary Partial European Search Report for European Patent Application No. 15776287.3 dated Sep. 29, 2017.
MiRBase-2012 [online]. [retrieved on Sep. 24, 2018]. Retrieved from the internet: <ftp://mirbase.org/pub/mirbase/19>. ,2012.
Anglicheau, et al., MicroRNA expression profiles predictive of human renal allograft status, Proc Natl Acad Sci U S A. 106(13) ,2009 ,5330-5335.
Bartel, et al., MicroRNAs: Genomics, Biogenesis, Mechanism, and Function, 2004, Cell, vol. 116, 281-297.
Bentwich, et al., Identification of hundreds of conserved and nonconserved human microRNAs, 2005, Nat Genet; 37: 766-770.
Chen, et al., Characterization of microRNAs in serum: a novel class of biomarkers for diagnosis of cancer and other diseases., Cell Research (2008) 18:997-1006.

(Continued)

*Primary Examiner* — Richard A Schnizer
(74) *Attorney, Agent, or Firm* — Saul Ewing LLP; Kathryn Doyle; Justin Crotty

(57) ABSTRACT

The present invention relates to the discovery that the expression levels of some microRNAs (miRNAs) can use a diagnostic signature to predict transplant outcomes in a transplant recipient. Thus, in various embodiments described herein, the methods of the invention relate to methods of diagnosing a transplant subject for acute rejection such as acute cellular rejection (ACR), methods of predicting a subject's risk of having or developing ACR and methods of assessing in a subject the likelihood of a successful or failure minimization of immunosuppression therapy (IST) dosage from standard ranges.

7 Claims, 5 Drawing Sheets
Specification includes a Sequence Listing.

(56) References Cited

OTHER PUBLICATIONS

Chen, et al., MicroRNAs modulate hematopoietic lineage differentiation., Science. Jan. 2, 2004;303(5654):83-6 (Abstract).
Danger, et al., Upregulation of miR-142-3p in Peripheral Blood Mononuclear Cells of Operationally Tolerant Patients with a Renal Transplant., 2012, J Am Soc Nephrol 23:597-606.
Ebert, et al., An endogenous positively selecting peptide enhances mature T cell responses and becomes an autoantigen in the absence of microRNA miR-181a., Nat Immunol. Nov. 2009 ; 10(11): 1162-1169.
Etheridge, et al., Extracellular microRNA: a new source of biomarkers, Mutat Res. Dec. 1, 2011; 717(1-2): 85-90.
Frank, et al., Clinical biomarkers in drug discovery and development., Nat Rev Drug Discov. Jul. 2003;2(7):566-80 (Abstract).
Friedman, et al., Most mammalian mRNAs are conserved targets of microRNAs., 2009, Genome Research 19:92-105.
Gilad, et al., Serum MicroRNAs Are Promising Novel Biomarkers., 2008, PLoS One 3(9): e3148.
Hanke, et al., A robust methodology to study urine microRNA as tumor marker: microRNA-126 and microRNA-182 are related to urinary bladder cancer., Urologic Oncology: Seminars and Original Investigations 28 (2010) 655-661.
Harris, et al., MicroRNAs as Immune Regulators: Implications for Transplanation., Am J Transplant. Apr. 2010 ; 10(4): 713-719.
He, et al., MicroRNAs: small RNAs with a big role in gene regulation., 2004, Nature Reviews Genetics 5, 522-531 (Abstract).
Kawai, et al., HLA-Mismatched Renal Transplantaton without Maintenance Immunosuppression., 2008, N Engl J Med 358(4):353-61.
Kim, et al., Genomics of microRNA., 2006, Trends Genet 22: 165-173 (Abstract).
Li, et al., miR-181a Is an Intrinsic Modulator of T Cell Sensitivity and Selection., Cell 129, 147-161, Apr. 6, 2007.
Lindsay, et al., microRNAs and the immune response, 2008, Trends Immunol; 29: 343-351 (Abstract).
Meltzer, et al., Small RNAs with big impacts, 2005, Nature 435:745-746.
Mitchell, et al., Circulating microRNAs as stable blood-based markers for cancer detection., PNAS Jul. 29, 2008 vol. 105 No. 30 10513-10518.
Rodriguez, et al., Requirement of bic/microRNA-155 for Normal Immune Function., Science. Apr. 27, 2007; 316(5824): 608-611.
Scholer, et al., Serum microRNAs as a novel class of biomarkers: a comprehensive review of the literature., 2010, Exp. Hematol 38: 1126-1130.
Sui, et al., Microarray analysis of MicroRNA expression in acute rejection after renal transplantation, Transpl Immunol. 19(1) ,Apr. 2008 ,81-85.
Van Huyen, et al., MicroRNAs as non-invasive biomarkers of heart transplant rejection, Eur Heart J. 35(45) , Dec. 2014 ,3194-3202.
Weber, et al., The MicroRNA Spectrum in 12 Body Fluids, Clin Chem. Nov. 2010 ; 56(11): 1733-1741.
Wehling, et al., "Translational medicine: can it really facilitate the transition of research from bench to bedside"?, Eur J Clin Pharmacol. Feb. 2006;62(2):91-5 (Abstract).
Farid, et al., "Hepatocyte-derived MicroRNAs as Serum Biomarkers of Hepatic Injury and Rejection after Liver Transplantation", Liver Transplantation, vol. 18, Mar. 2012, 290-297.
Hu, et al., "Plasma MicroRNA, a Potential Biomarker for Acute Rejection After Liver Transplantation", Transplantation, vol. 95, No. 8, Apr. 2013, 991-999.
Chen, et al., "Reproducibility of quantitative RT-PCR array in miRNA expression profiling and comparison with microarray analysis," BMC Genomics. 10 ,Aug. 1-10, 2009.

\* cited by examiner

USE OF MICRO-RIBONUCLEIC ACID (miRNA) TO DIAGNOSE TRANSPLANT REJECTION AND TOLERANCE OF IMMUNOSUPPRESSION THERAPY

CROSS REFERENCE TO RELATED APPLICATIONS

This application is a continuation of, and claims priority to, U.S. patent application Ser. No. 15/302,815, filed Oct. 7, 2016, which is a 35 U.S.C. § 371 national phase application from, and claims priority to, International Application No. PCT/US2015/025382, filed Apr. 10, 2015, and published under PCT Article 21(2) in English, which claims priority to and the benefit of U.S. Provisional Application No. 61/977,980, filed Apr. 10, 2014, all of which applications are incorporated herein by reference in their entireties.

STATEMENT REGARDING FEDERALLY SPONSORED RESEARCH OR DEVELOPMENT

This invention was made with government support under A1063589 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 26, 2019, is named 046483-7006US2 Sequence Listing.txt and is 28.2 kilobytes in size.

BACKGROUND OF THE INVENTION

Solid organ transplantation provides life-saving therapy for patients with end-stage organ disease. In 2010, a total of 28,664 transplants were performed in the U.S., including 16,899 kidney, 6291 liver, 2333 heart, and 1770 lung transplants (Engels et al., 2011, JAMA, 306(17): 1891-1901). Although there has been significant improvements in immunosuppressant therapies and in patient treatment pre- and post-transplant surgery, rejection of graft still affects approximately 60% of transplanted individuals and is thus still major risk factors of graft loss with rejection observed in up to 40% of transplanted individuals within the first year post-transplant (Jain et al., 2000, Ann Surg. 232(4): 490-500). Acute rejection is also a known risk factor for progressing to chronic rejection and thus detection and treatment of acute rejection episodes as early as possible is a major goal to minimize graft damage and to stem downstream rejection episodes. In most cases, adaptive immune responses to the grafted tissues are the major impediment to successful transplantation. Rejection is caused by immune responses to alloantigens on the graft, which are proteins that vary from individual to individual within a species and are therefore perceived as foreign by the recipient. (Janeway, et al., 2001, Immunobiology: The Immune System in Health and Disease. 5th edition. New York: Garland Science).

Current monitoring and diagnostic tools are limited in their ability to diagnose acute rejection at early stages e.g. acute kidney allograft rejection is currently diagnosed following needle core biopsy of the graft, a highly invasive procedure precipitated by crude biomarkers such as an increase in the levels of creatinine in a recipients serum (Girlanda et al., 2007, Semin Nephrol. Jul; 27(4):462-78). Serum creatinine levels lack the sensitivity and specificity required to effectively predicting rejection yet it remains the best surrogate markers of acute rejection (Zhou et al., 2006, Nephrol Self Assess Program. 5(2): 63-71). In liver transplantation, the presence of elevated levels of aspartate transferase (AST) and alanine transferase (ALT) are used as an indicator to assess liver damage (Giboney, 2005, Am Fam Physician 71 (6): 1105-10). However, a level of more than three times of normal may also be due to include alcohol toxicity, viral hepatitis, liver cancer, sepsis, Wilson disease, autoimmune hepatitis and drug toxicity (Giboney, 2005, Am Fam Physician 15; 71(6):1105-1110; Raurich et al., 2009, Hepatol. Res. 39 (7): 700-5.)

The development of a methodology to allow rapid diagnosis of early allograft rejection including but not limited to kidney, heart, lung, liver, pancreas, bone, bone marrow, bowel, nerve, stem cells, transplants derived from stem cells as well as tissue component and tissue composites, would be a major advancement in the field. Allograft biopsies are currently highly invasive and are plagued by a number of complications including bleeding of the site of puncture, shock, allograft fistulas, and even graft loss and the biopsy procedure carries a greater risk in children. The availability of a non-invasive diagnostic test with high sensitivity and specificity to inform clinicians regarding the status of the patient's rejection trajectory would be of considerable value.

Over the last decade advances in surgical techniques, immunosuppressive therapies and infectious monitoring and treatment have revolutionized patient and graft survival. However, despite this success, transplant recipients still exhibit much higher morbidity and mortality than the general population. Although this is in part due to the effects of chronic allograft injury, the main causes are comorbidities influenced by chronic immunosuppressive drug usage (Soulillou and Giral 2007, Transplantation 72 (Suppl 12): S89-93; Hourmant et al., 1998, Lancet 351: 623-628; Halloran, 2004, N Engl J Med 351: 2715-2729).

Immunosuppression related toxicities can be significant. For instance, several studies in adult liver transplant recipients, have shown a time-dependent continuous decline in renal function with exposure to immunosuppressive therapy. Other important complications of long term immunosuppression include new onset of diabetes after transplantation (NODAT), hypertension, hyperlipidemia and the need for statin therapy (Srinivas et al., 2008, CJASN: (Supplement 2) S101-S116). To redress this situation, research priorities in organ transplantation are moving away from the search of novel powerful immunosuppressive drugs toward the identification of strategies to minimize immunosuppression.

Biomarkers can be used to determine the propensity to develop a disease, measure its progress, or predict prognosis (Wehling, 2006, Eur. J. Clin. Pharmacol, 62:91-95). In clinical trials, biomarkers can help in patient stratification and thereby increase the chances of a successful outcome by targeting the appropriate population. In addition, biomarkers can pave the way to individualize treatment and thereby usher in a new era in personalized medicine (Frank et al., 2003, Nat. Rev. Drug Discov. 2:566-580). Incorporation of molecular biomarkers into immunosuppression treatments can have large benefits such as the avoidance of invasive biopsies as well as individualized guidance of minimization resulting in reductions in drug-related toxicities.

MicroRNAs (miRNAs) are small non-coding RNA molecules of about 22 nucleotides that regulate the posttranscriptional expression of target genes (Bartel, 2004, Cell 116: 281-297). The biogenesis of miRNA is a multistep process occurring in the cell nucleus and cytoplasm. The mature miRNA is incorporated into the RNA-induced silencing complex to bind the 3' untranslated region (UTR) of mRNA, leading to mRNA degradation or translational inhibition (Kim et al., 2006, Trends Genet 22: 165-173). To date over 1000 human miRNAs have been identified although the target genes of many remain unknown (Bentwich et al., 2005, Nat Genet; 37: 766-770; Friedman et al., 2009, Genome Res 19: 92-105). miRNAs have been shown to play crucial roles in cellular development, cell differentiation, tumorigenesis, apoptosis and proliferation (He et al., 2004, Nat Rev Genet. 5: 522-531; Meltzer, 2005. Nature; 435: 745-746; Chen et al., 2004, Science; 303: 83-86.). Further, miRNAs are involved in innate and adaptive immune responses (Harris et al., 2010, Am J Transplant; 10: 713-719; Lindsay, 2008, Trends Immunol; 29: 343-351.). For example, miR-181a is an intrinsic modulator of T-cell sensitivity and selection that facilitates clonal deletion by modulating the T-cell receptor (TCR) signaling threshold of thymocytes (Li et al., 2007, Cell 129: 147-161; Ebert et al., 2009, Nat Immunol; 10: 1162-1169.). miR-155 is important for cytokine production by T and B cells and antigen presentation by dendritic cells (Rodriguez et al., 2007, Science; 316: 608-611.). Thus miRNAs as immune regulators may govern expression of genes relevant to allograft rejection, tolerance induction and posttransplant infection in recipients of organ transplants (Harris et al., 2010, Am J Transplant; 10:713-719). Recent studies have demonstrated differential expression of miRNAs after clinical renal transplantation. It was recently demonstrated that miRNAs are present in the serum and plasma of humans and other mammals, such as rats, mice, cows and horses (Chen et al., 2008, Cell Res. 18:997-1006; Mitchell et al., 2008, Proc. Natl. Acad. Sci. USA 105: 10513-10518). This finding opens up the feasibility of using miRNAs as biomarkers of disease. Further evidence for the presence of miRNAs in body fluids came from an analysis of urine samples (Gilad et al., 2008, PLoS One 3:e3148). Four miRNAs were significantly elevated in urine from urothelial bladder cancer patients, demonstrating the utility of miRNAs as a noninvasive diagnostic option (Hanke et al, 2009, Urol. Oncol). All of these studies illustrate the potential use of miRNAs as novel biomarkers amenable to clinical diagnosis in translational medicine (Gilad et al, 2008, PLoS One 3:e3148; Weber et al, 2010, Clin. Chem. 56: 1733-1741; Etheridge et al, 2011, Mutat. Res.; Scholer et al, 2010, Exp. Hematol 38: 1126-1130).

There is a great need in the art for methods for detecting and quantifying miRNA expression for the diagnosis of transplant rejection and tolerance of immunosuppression therapy in a patient. Furthermore, there is a need in the art for a non-invasive diagnostic test with strong sensitivity and selectivity to inform clinicians regarding the status of the patient's rejection trajectory to provide the best treatment modalities. The present invention satisfies these needs.

SUMMARY OF THE INVENTION

The invention includes a method for detecting or predicting transplant rejection of a transplanted organ in a subject. This method comprises determining a level of at least one miRNA expression in a sample from the subject, comparing the level of at least one miRNA in the sample from the subject relative to a baseline level in a control wherein a difference in the level of the at least one miRNA in the sample from the level of the at least one miRNA in the control is indicative of an acute transplant rejection, and further wherein when acute transplant rejection is indicated, treatment for the rejection is recommended.

The invention also includes a method for predicting minimization of immunosuppression therapy (IST) in a transplant subject. This method comprises determining a level of at least one miRNA expression in a sample from the subject, comparing the level of at least one miRNA in the sample from the subject relative to a baseline level in a control wherein a difference in the level of the least one miRNA in the sample from the level of the at least one miRNA in the control is indicative of likelihood of success or failure of IST minimization, and further wherein when failure of IST minimization is indicated, treatment of the subject is recommended.

The invention further includes a composition for detecting or predicting transplant rejection of a transplanted organ in a subject comprising a plurality of miRNAs consisting of SEQ ID NOs: 1-23.

The invention further includes a composition for detecting or predicting transplant rejection of a transplanted organ in a subject comprising a plurality of miRNAs consisting of SEQ ID NOs: 1-23 and 97-134.

The invention further includes kit comprising a plurality of oligonucleotides that are configured to detect at least one miRNA from selected from the group consisting of SEQ ID NOs: 1-23 and 97-134.

The invention further includes a composition for detecting or predicting the ability, or non-ability, of minimizing IST dosage in a subject post-transplantation comprising a plurality of miRNAs consisting of SEQ ID NOs: 6-8, 22, 24-48.

The invention further includes kit comprising a plurality of oligonucleotides that are configured to detect at least one miRNA from the group consisting of SEQ ID NOs: 6-8, 22, 24-48.

In some embodiments, the acute transplant rejection comprises acute cellular rejection (ACR). In some embodiments, the at least one miRNA for detecting or predicting transplant rejection of a transplanted organ in a subject is selected from the group consisting of SEQ ID NOs: 1-3. In other embodiments, the at least one miRNA for detecting or predicting transplant rejection of a transplanted organ in a subject is selected from the group consisting of SEQ ID NOs: 4-15. In further embodiments, the at least one miRNA for detecting or predicting transplant rejection of a transplanted organ in a subject is selected from the group consisting of SEQ ID NOs: 16-23.

In yet further embodiments, the at least one miRNA for detecting or predicting transplant rejection of a transplanted organ in a subject is selected from the group consisting of SEQ ID NOs: 1-23. In yet further embodiments, the at least one miRNA for detecting or predicting transplant rejection of a transplanted organ in a subject is selected from the group consisting of SEQ ID NOs: 1-23 and 97-134. In some embodiments, the at least one miRNA for predicting minimization of immunosuppression therapy (IST) in a transplant subject is selected from the group consisting of SEQ ID NOs: 24-26. In other embodiments, the at least one miRNA for predicting minimization of immunosuppression therapy (IST) in a transplant subject is selected from the group consisting of SEQ ID NOs: 6-8, 22, 27-48. In other embodiments, the at least one miRNA for predicting minimization of immunosuppression therapy (IST) in a transplant subject is selected from the group consisting of SEQ ID NOs: 6-8, 22, 24-48. In some embodiments, the minimization of IST is lower than the initial dosage by at least 75%. In certain embodiments, the minimization of IST is lower than the initial dosage by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by at least 100%.

In some embodiments, the level of the at least one miRNA is higher than the level of the at least one miRNA in the control by at least 1 fold. In other embodiments, determining the level of the at least one miRNA employs at least one technique selected from the group consisting of reverse transcription, PCR, microarray, and Next Generation Sequencing. In further embodiments, the sample is at least one selected from the group consisting of urine, peripheral blood, serum, bile, bronchoalveolar lavage (BAL) fluid, pericardial fluid, gastrointestinal fluids, stool samples, biological fluid gathered from an anatomic area in proximity to an allograft, and biological fluid from an allograft. In further embodiments, the transplanted organ is at least one selected from the group consisting of heart, liver, lung, kidney, an intestine, pancreas, pancreatic islet cells, eye, skin, and stem cells. In further embodiments, the comparison of level of miRNA expression is computed in a regression model to indicate a trajectory of acute rejection of the transplanted organ. In some embodiments, the kit's oligonucleotides are configured to detect at least SEQ ID NOs: 1-3. In other embodiments, at least one of kit's oligonucleotides is selected from the group consisting of SEQ ID NOs: 49-71 and 135-172. In other embodiments, the kit's oligonucleotides are configured to detect at least SEQ ID NOs: 24-26. In yet other embodiments, at least one of the kit's oligonucleotides is selected from the group consisting of SEQ ID NOs: 53-55, 70, 72-96. In some embodiments, the subject is a mammal. In other embodiments, the mammal is a human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

Figure 1:
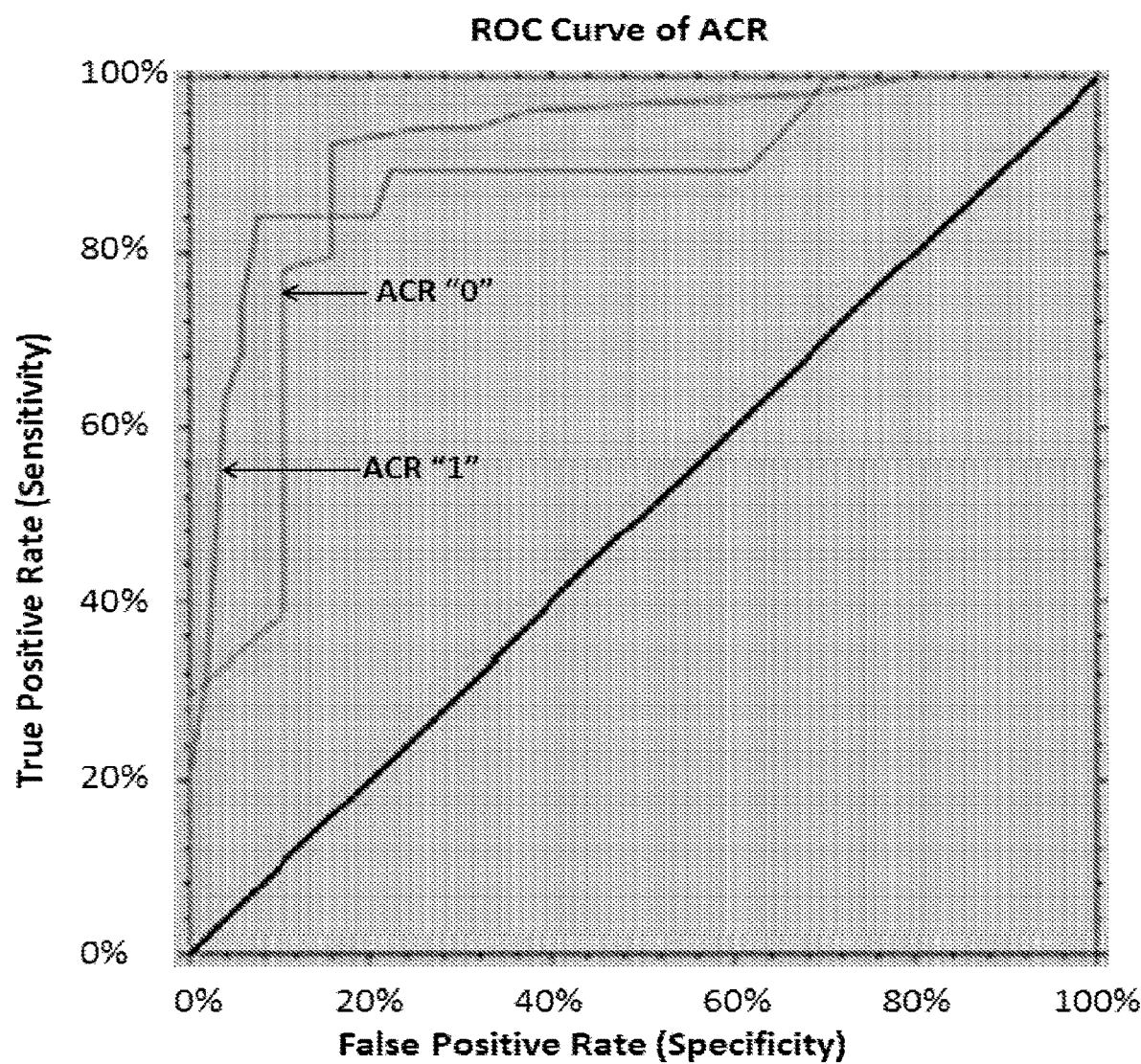
FIG. 1 is a graph illustrating a receiver operating characteristic (ROC) plot that outlines the fraction of true positives out of the total actual positives (TPR=true positive rate) versus the fraction of false positives out of the total actual negatives (FPR=false positive rate). This plot represents the 3-miRNA serum ACR diagnosis signature (hsa-miR-125b, hsa-miR-100 and hsa-miR-483).

The present invention relates to the discovery that the expression levels of some microRNAs (miRNAs) can be used as diagnostic signature to predict transplant outcomes in a transplant recipient. Thus, in various embodiments described herein, the methods of the invention relate to methods of diagnosing a transplant subject for acute rejection such as acute cellular rejection (ACR), methods of predicting a subject's risk of having or developing ACR and methods of assessing if a subject is prone to a successful or failure reduction the immunosuppression therapy (IST) dosage from standard ranges.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0, 1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The terms "dysregulated" and "dysregulation" as used herein describes a decreased (down-regulated) or increased (up-regulated) level of expression of a miRNA present and detected in a sample obtained from subject as compared to the level of expression of that miRNA present in a control sample, such as a control sample obtained from one or more normal, not-at-risk subjects, or from the same subject at a different time point. In some instances, the level of miRNA expression is compared with an average value obtained from more than one not-at-risk individuals. In other instances, the level of miRNA expression is compared with a miRNA level assessed in a sample obtained from one normal, not-at-risk subject.

"Differentially increased expression" or "up regulation" refers to expression levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments therebetween, than a control.

"Differentially decreased expression" or "down regulation" refers to expression levels which are at least 10% or more, for example, 20%, 30%, 40%, or 50%, 60%, 70%, 80%, 90% lower or less, and/or 2.0 fold, 1.8 fold, 1.6 fold, 1.4 fold, 1.2 fold, 1.1 fold or less lower, and any and all whole or partial increments therebetween, than a control.

The term "expression" as used herein is defined as the transcription and/or translation of a particular nucleotide sequence.

As used herein, "isolated" means altered or removed from the natural state through the actions, directly or indirectly, of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

As used herein, "microRNA" or "miRNA" describes miRNA molecules, generally about 15 to about 50 nucleotides in length, preferably 17-23 nucleotides, which can play a role in regulating gene expression through, for example, a process termed RNA interference (RNAi). RNAi describes a phenomenon whereby the presence of an RNA sequence that is complementary or antisense to a sequence in a target gene messenger RNA (mRNA) results in inhibition of expression of the target gene. miRNAs are processed from hairpin precursors of about 70 or more nucleotides (pre-miRNA) which are derived from primary transcripts (pri-miRNA) through sequential cleavage by RNAse III enzymes.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

The term, "polynucleotide" includes cDNA, RNA, DNA/RNA hybrid, anti-sense RNA, siRNA, miRNA, snoRNA, genomic DNA, synthetic forms, and mixed polymers, both sense and antisense strands, and may be chemically or biochemically modified to contain non-natural or derivatized, synthetic, or semisynthetic nucleotide bases. Also, included within the scope of the invention are alterations of a wild type or synthetic gene, including but not limited to deletion, insertion, substitution of one or more nucleotides, or fusion to other polynucleotide sequences.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

The term "spiked-in" refers to a defined sequence nucleic acid species (such as a RNA species, sequence or transcript) that is added to a sample during processing and used to assess the performance of a microarray. "Spiked-in" refers to artificial sequences that can include standard or modified nucleotides such as locked nucleic acids (LNAs), peptide nucleic acids (PNA), or nucleic acid analogues (e.g., isoG, isoC, etc.). In some embodiments, the defined sequence nucleic acid comprises a sequence that is not likely to be found in the biological sample to be analyzed and is selected to have minimal self-hybridization and cross hybridization with other similar sequences in the set. Such spiked-in controls can be used to monitor microarray quality, in terms of dynamic range, reproducibility, etc. Different spiked-in controls can be used to monitor different processes in a microarray analysis. In some embodiments, the measured degree of hybridization between the spiked-in and the control probes is used to calibrate and normalize the hybridization measurements of the sample RNA or miRNA.

As used herein, "hybridization," "hybridize (s)" or "capable of hybridizing" is understood to mean the forming of a double or triple stranded molecule or a molecule with partial double or triple stranded nature. Complementary sequences in the nucleic acids pair with each other to form a double helix. The resulting double-stranded nucleic acid is a "hybrid." Hybridization may be between, for example two complementary or partially complementary sequences. The hybrid may have double-stranded regions and single stranded regions. The hybrid may be, for example, DNA:DNA, RNA:DNA or DNA:RNA. Hybrids may also be formed between modified nucleic acids (e.g., LNA compounds). One or both of the nucleic acids may be immobilized on a solid support. Hybridization techniques may be used to detect and isolate specific sequences, measure homology, or define other characteristics of one or both strands. The stability of a hybrid depends on a variety of factors including the length of complementarity, the presence of mismatches within the complementary region, the temperature and the concentration of salt in the reaction or nucleotide modifications in one of the two strands of the hybrid.

A "nucleic acid probe," or a "probe", as used herein, is a DNA probe or an RNA probe.

The term "Next-generation sequencing" (NGS), also known as high-throughput sequencing, is used herein to describe a number of different modern sequencing technologies that allow to sequence DNA and RNA much more quickly and cheaply than the previously used Sanger sequencing (Metzker, 2010, Nature Reviews Genetics 11.1: 31-46). It is based on micro- and nanotechnologies to reduce the size of sample, the reagent costs, and to enable massively parallel sequencing reactions. It can be highly multiplexed which allows simultaneous sequencing and analysis of millions of samples. NGS includes first, second, third as well as subsequent Next Generations Sequencing technologies.

"Sample" or "biological sample" as used herein means a biological material from a subject, including but is not limited to organ, tissue, exosome, blood, plasma, saliva, urine and other body fluid, A sample can be any source of material obtained from a subject.

The terms "subject," "patient," "individual," and the like are used interchangeably herein, and refer to any animal, or cells thereof whether in vitro or in situ, amenable to the methods described herein. In certain non-limiting embodiments, the patient, subject or individual is a human. Non-human mammals include, for example, livestock and pets, such as ovine, bovine, porcine, canine, feline and murine mammals. Preferably, the subject is human. The term "subject" does not denote a particular age or sex. Preferably the subject is a human patient. In some embodiments, the subject is a human having received an organ transplant.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2,7, 3, 4, 5, 5.3, and 6. This applies regardless of the breadth of the range.

A "mutation" as used therein is a change in a DNA sequence resulting in an alteration from its natural state. The mutation can comprise deletion and/or insertion and/or duplication and/or substitution of at least one deoxyribonucleic acid base such as a purine (adenine and/or thymine) and/or a pyrimidine (guanine and/or cytosine) Mutations may or may not produce discernible changes in the observable characteristics (phenotype) of an organism (subject).

The term "biopsy" refers to a specimen obtained by removing tissue from living patients for diagnostic examination. The term includes aspiration biopsies, brush biopsies, chorionic villus biopsies, endoscopic biopsies, excision biopsies, needle biopsies (specimens obtained by removal by aspiration through an appropriate needle or trocar that pierces the skin, or the external surface of an organ, and into the underlying tissue to be examined), open biopsies, punch biopsies (trephine), shave biopsies, sponge biopsies, and wedge biopsies. Biopsies also include a fine needle aspiration biopsy, a minicore needle biopsy, and/or a conventional percutaneous core needle biopsy.

"Baseline expression" or "Baseline level of gene expression level" includes the particular gene expression level of a healthy subject or a subject with a well-functioning transplant. The baseline level of gene expression includes the gene expression level of a subject without acute rejection. The baseline level of gene expression can be a number on paper or the baseline level of gene expression from a control sample of a healthy subject or a subject with a well-functioning transplant.

"Acute rejection" or "acute cellular rejection" refers to an immune reaction evoked by allografted organs. In general, the acute rejection has its onset 2-60 days after transplantation. and possibly other cell-specific antigens expressed by the tubular epithelium and vascular endothelium. It is caused by mismatched HLA antigens, and possibly other cell-specific antigens expressed by the tubular epithelium and vascular endothelium. It is believed that both delayed hypersensitivity and cytotoxicity mechanisms are involved. Acute rejection is characterized by infiltration of the transplanted tissue by immune cells of the recipient, which carry out their effector function and destroy the transplanted tissue. It can be characterized by interstitial vascular endothelial cell swelling, interstitial accumulation of lymphocytes, plasma cells, immunoblasts, macrophages, neutrophils; tubular separation with edema/necrosis of tubular epithelium; swelling and vacuolization of the endothelial cells, vascular edema, bleeding and inflammation, renal tubular necrosis, sclerosed glomeruli, tubular 'thyroidization'.

"Chronic rejection" generally occurs within several months to years after engraftment, even in the presence of successful immunosuppression of acute rejection. Fibrosis is a common factor in chronic rejection of all types of organ transplants. Chronic rejection can typically be described by a range of specific disorders that are characteristic of the particular organ. For example, in lung transplants, such disorders include fibroproliferative destruction of the airway (bronchiolitis obliterans); in heart transplants or transplants of cardiac tissue, such as valve replacements, such disorders include fibrotic atherosclerosis; in kidney transplants, such disorders include, obstructive nephropathy, nephrosclerorsis, tubulointerstitial nephropathy; and in liver transplants, such disorders include disappearing bile duct syndrome. Chronic rejection can also be characterized by ischemic insult, denervation of the transplanted tissue, hyperlipidemia and hypertension associated with immunosuppressive drugs.

The term "transplant rejection" encompasses both acute and chronic transplant rejection.

The term "diagnosis" is used herein to refer to the identification or classification of a molecular or pathological state, disease or condition. For example, "diagnosis" may refer to identification of a particular type of acute rejection, e.g., acute cellular rejection.

The term "prediction" is used herein to refer to the likelihood that a patient will develop acute rejection. Thus, prediction also includes the time period without acute rejection.

As used herein, the term "transplantation" refers to the process of taking a cell, tissue, or organ, called a "transplant" or "graft" from one individual and placing it or them into a (usually) different individual. The individual who provides the transplant is called the "donor" and the individual who received the transplant is called the "host" (or "recipient"). An organ, or graft, transplanted between two genetically different individuals of the same species is called an "allograft". A graft transplanted between individuals of different species is called a "xenograft".

As used herein, "transplant rejection" refers to a functional and structural deterioration of the organ due to an active immune response expressed by the recipient, and independent of non-immunologic causes of organ dysfunction. Acute transplant rejection can result from the activation of recipient's T cells and/or B cells; the rejection primarily due to T cells is classified as T cell mediated acute rejection or acute cellular rejection (ACR) and the rejection in which B cells are primarily responsible is classified as antibody mediated acute rejection (AMR). In some embodiments, the methods and compositions provided can detect and/or predict acute cellular rejection.

As used herein, the terms "immunosuppression" or "immunosuppressive therapy (IST)" involve an act that reduces the activation or efficacy of the immune system. Deliberately induced immunosuppression is performed to prevent the body from rejecting an organ transplant, treating graft-versus-host disease after a bone marrow transplant, or for the treatment of auto-immune diseases such as rheumatoid arthritis or Crohn's disease.

As used herein, the term "tolerance" is a state of immune unresponsiveness specific to a particular antigen or set of antigens induced by previous exposure to that antigen or set.

Tolerance is generally accepted to be an active process and, in essence, a learning experience for T cells. Tolerance, as used herein, refers to the inhibition of a graft recipient's ability to mount an immune response which would otherwise occur, e.g., in response to the introduction of a nonself MHC antigen into the recipient. Tolerance can involve humoral, cellular, or both humoral and cellular responses.

As used herein, the term "biomarker" includes a polynucleotide or polypeptide molecule which is present or increased in quantity or activity in subjects having acute rejection or where the acute rejection is anticipated.

As used herein, the term "biomarkers for diagnosis" or "diagnosis signature" includes a group of markers such as miRNA, the quantity or activity of each member of which is correlated with subjects having acute rejection or where the acute rejection is anticipated. In certain embodiments, the diagnosis signature may include only those markers. In some embodiments, the signature includes one, two, three, four, five, six, seven, eight, or nine or more miRNAs.

As used herein, the term "biomarkers for tolerance" or "tolerance signature" includes a group of markers such as miRNA, the quantity or activity of each member of which is correlated with subjects having tolerance for a certain level of immunosuppression minimization or where the immunosuppression minimization is anticipated. In certain embodiments, the tolerance signature may include only those markers. In some embodiments, the signature includes one, two, three, four, five, six, seven, eight, or nine or more miRNAs.

Methods of the Invention

The invention relates to the unexpected discovery that it is possible to anticipate the future development of acute cellular rejection with a high degree of accuracy; and diagnose acute cellular rejection with a high degree of sensitivity and specificity without performing a transplant biopsy, by measuring the levels certain microRNAs, referred as "ACR diagnosis signature", in serum samples from liver transplant recipients. Furthermore, by measuring the level of other microRNAs candidates, referred as "IST tolerance signature", the invention enables the prediction in a transplant subject of the success or failure of minimizing immunosuppression therapy (IST) dosage from standard ranges.

In some embodiments, miRNAs associated with ACR are differentially expressed. In yet other embodiments, miRNAs associated with failure in minimizing IST are differentially expressed. Thus, the invention relates to compositions and methods useful for the detection and quantification of miRNAs and the use of these miRNAs signature for the diagnosis, assessment, and characterization of trajectory of, and transplant-outcomes, as well as the adjustment of IST dosage in a subject in need thereof.

Reference Amount of Expression of the miRNA Marker(s)

The method of the invention includes comparing a measured amount of expression of a miRNA marker(s) in a biological sample from a subject to a reference amount (i.e. the control) of expression of a miRNA marker(s).

Reference for Detecting or Predicting Acute Cellular Rejection

In one embodiment, the reference (i.e. the control) level of expression of the miRNA(s) may be obtained by measuring the expression level of a miRNA in a subject having a non-rejected organ. For example, the subject having a non-rejected organ may include a healthy subject. Preferably, the healthy subject is a subject of similar age, gender, race, graft-donor source, Banff histologic grade, and/or that underwent the same initial anti-rejection treatment as the patient having a transplanted organ for which risk of organ failure is to assessed.

Another example of a subject having a non-rejected organ is a subject having a well-functioning transplanted organ. A well-functioning (e.g., stable) transplanted organ is defined as a transplanted organ that does not exhibit organ failure (e.g., rejection). Preferably, a well-functioning transplanted organ is a transplanted organ that has not developed transplant dysfunction or morphologic evidence of transplant injury in areas of the transplant. Preferably, the subject having a well-functioning (e.g., stable) transplanted organ is a subject of similar age, gender, race, graft-donor source, Banff histologic grade, and/or that underwent the same initial anti-rejection treatment as the subject having a transplanted organ for which risk of organ failure is to be assessed.

In another embodiment, the reference amount is obtained by measuring an amount of expression of the miRNA in a second biological sample from the subject. For example, the second biological sample may be obtained from the subject before the organ transplantation and/or from another non-rejected organ of the subject.

In yet another embodiment, the reference amount of expression of the miRNA is a value for expression of the miRNA that is accepted in the art (e.g., spiked-in).

Reference for Predicting Success or Failure of Minimizing Immunosuppression Therapy (IST).

In one embodiment, the reference amount of expression of the miRNA is obtained by measuring an amount of expression of the miRNA in a transplant subject having a successful tolerance for a decrease in the IST dosage. For example, the subject under a lower IST dosage includes a healthy subject. Preferably, the healthy subject is a subject of similar age, gender, race, graft-donor source, Banff histologic grade, and/or that underwent the same initial anti-rejection treatment as the subject having a transplanted organ for which the minimization of IST is to assessed.

Another example of a subject having a non-rejected organ is a subject having a well-functioning transplanted organ. A well-functioning (e.g., stable) transplanted organ may be defined as a transplanted organ that does not exhibit organ failure (e.g., rejection). Preferably, a well-functioning transplanted organ is a transplanted organ that has not developed transplant dysfunction or morphologic evidence of transplant injury in areas of the transplant. Preferably, the subject having a well-functioning (e.g., stable) transplanted organ is a subject of similar age, gender, race, graft-donor source, Banff histologic grade, and/or that underwent the same initial anti-rejection treatment as the subject having a transplanted organ for which risk of organ failure is to assessed.

In another embodiment, the reference amount is obtained by measuring an amount of expression of the miRNA in a second biological sample from the subject. For example, the second biological sample may be obtained from the subject before the organ transplantation and/or from another non-rejected organ of the subject.

In another embodiment, the reference amount is obtained by measuring an amount of expression of said miRNA in a second biological sample from the subject prior the organ transplantation and/or prior beginning IST treatment and/or prior beginning minimizing IST.

In yet another embodiment, the reference amount of expression of the miRNA is a value for expression of the miRNA that is accepted in the art (e.g., spiked-in).

Comparison of the Measured Amount of Expression of the miRNA marker

The method includes comparing the measured amount of expression of the miRNA to the reference amount of expression of the miRNA.

For Detecting or Predicting Acute Cellular Rejection

The miRNA marker may be, for example, a miRNA selected from hsa-miR-125b-5p, hsa-miR-100-5p, hsa-miR-483-5p, hsa-miR-885-5p, hsa-miR-122-5p, hsa-miR-99a-5p, hsa-miR-30a-5p, hsa-miR-497-5p, hsa-miR-194-5p, hsa-miR-34a-5p, hsa-miR-192-5p, hsa-miR-215, hsa-miR-375, hsa-miR-193a-5p, hsa-miR-483-5p, hsa-miR-505-3p, hsa-miR-378a-3p, hsa-miR-193b-3p, hsa-miR-874, hsa-miR-365a-3p, hsa-miR-152, hsa-miR-148a-3p and hsa-miR-29a-5p, or any combination thereof.

In one embodiment, the miRNA marker is selected from hsa-miR-125b-5p, hsa-miR-100-5p, hsa-miR-483-5p, hsa-miR-885-5p, hsa-miR-122-5p, hsa-miR-99a-5p, hsa-miR-30a-5p, hsa-miR-497-5p, hsa-miR-194-5p, hsa-miR-34a-5p, hsa-miR-192-5p, hsa-miR-215, hsa-miR-375, hsa-miR-193a-5p and hsa-miR-483-5p, or any combination thereof.

In another embodiment, the miRNA marker is hsa-miR-125b-5p, hsa-miR-100-5p and hsa-miR-483-5p, wherein an increase of expression of the miRNA marker that is equivalent to at least about 1-fold as compared to the reference amount of expression of the miRNA marker indicates an increased risk of rejection of the transplanted organ.

An increase of expression that is equivalent to at least about 1-fold may be an increase in an amount equivalent to at least about 1-, 2-, 3-, 4-, 5-, 6-, 7-, 8-, 9-, 10-, 11-, 12-, 13-, 14-, 15-, 16-, 17-, 18-, 19-, 20-fold, or more and any and all partial integers therebetween, as compared with the increase in the reference amount of expression of the miRNA marker. Examples of methods to quantify an increase of expression are known in the art, as are described in the Examples disclosed elsewhere herein.

For Predicting Success or Failure of Minimizing Immunosuppression Therapy (IST).

The miRNA marker may be, for example, a miRNA selected from hsa-miR-146b-5p, hsa-miR-424-3p, hsa-miR-125a-5p, hsa-miR-342-3p, hsa-miR-150-5p, hsa-miR-421, hsa-miR-148a-3p, hsa-miR-223-5p, hsa-miR-495-3p, hsa-miR-497-5p, hsa-miR-29a-3p, hsa-miR-30a-5p, hsa-miR-374b-5p, hsa-let-7g-5p, hsa-miR-99a-5p, hsa-miR-18b-5p, hsa-miR-7-1-3p, hsa-miR-181c-5p, hsa-miR-454-3p, hsa-miR-485-3p, hsa-miR-374a-5p, hsa-miR-99b-5p, hsa-miR-192-5p, hsa-miR-191-5p, hsa-miR-21-5p, hsa-miR-24-3p, hsa-miR-27b-3p, hsa-miR-222-3p, hsa-miR-20a-3p and hsa-miR-106b-5p, or any combination thereof.

In one embodiment, the miRNA marker is hsa-miR-146b-5p, hsa-miR-424-3p and hsa-miR-125a-5p, wherein an increase of expression of the miRNA marker that is equivalent to at least about 1-fold as compared to the reference amount of expression of the miRNA marker indicates an increased risk of failing minimization of IST.

An increase of expression that is equivalent to at least about 1-fold may be an increase in an amount equivalent to at least about 1-, 2-, 3-, 4-, 5-, 6-, 7-, 8-, 9-, 10-, 11-, 12-, 13-, 14-, 15-, 16-, 17-, 18-, 19-, 20-fold, or more, and any and all partial integers therebetween, as compared with the increase in the reference amount of expression of the miRNA marker. Preferably, the increase is a fold value. Examples of methods to quantify an increase of expression are known in the art, as are described in the Examples disclosed elsewhere herein.

Normalization

In one embodiment, the invention includes normalizing the amount of expression of the miRNA marker. The method includes measuring an amount of expression of commercially available spiked-in markers as references against the expression level of miRNA from the subject.

For Detecting or Predicting Acute Cellular Rejection

The method further includes measuring an amount of expression of a miRNA marker in a biological sample from a first subject having a rejected organ or at risk for rejecting an organ. The method further includes measuring an amount of expression of miRNA marker in a biological sample from a second subject having a non-rejected organ. In addition, the method includes comparing the measured amount of the miRNA markers between these two types of subjects. Furthermore, when acute transplant rejection is indicated, treatment for the rejection is recommended.

When the level of miRNAs in the first subject is greater than the level of miRNAs in second subject by an amount equivalent to at least 1-fold, the calculation indicates an increased risk of rejection of the transplanted organ in the subject having a transplanted organ. The calculated increase that is at least 1-fold may be an increase that is equivalent to at least about 1-, 2-, 3-, 4-, 5-, 6-, 7-, 8-, 9-, 10-, 11-, 12-, 13-, 14-, 15-, 16-, 17-, 18-, 19-, 20-fold, or more and any and all partial integers therebetween.

When the level of miRNAs in the first subject is greater than the level of miRNAs in second subject by an amount equivalent to less than 1-fold, the calculation indicates an increased risk of rejection of the transplanted organ in the subject having a transplanted organ. The calculated increase that is less than 1-fold may be an increase that is equivalent to at most about 0.9-, 0.8-, 0.7-, 0.6-, 0.5-, 0.4-, 0.3-, 0.2-, or 0.1-fold, or less.

For Predicting Success or Failure of Minimizing Immunosuppression Therapy (IST).

The method further includes measuring an amount of expression of an endogenously expressed small non-coding reference RNA in a biological sample from a first tested subject under consideration for minimization of IST dosage. The method further includes measuring an amount of expression of miRNA marker in a biological sample from a second subject having a successful minimization of IST dosage. In addition, the method includes comparing the measured amount of the miRNA marker between these two types of subjects. Furthermore, when failure of IST minimization is indicated, treatment of the subject is recommended.

When the level of miRNAs in the first subject is greater than the level of miRNAs in second subject by an amount equivalent to at least 1-fold, the calculation indicates an increased risk of failing minimization of IST dosage in a subject under IST treatment. The calculated increase that is at least 1-fold may be an increase that is equivalent to at least about 1-, 2-, 3-, 4-, 5-, 6-, 7-, 8-, 9-, 10-, 11-, 12-, 13-, 14-, 15-, 16-, 17-, 18-, 19-, 20-fold, or more and any and all partial integers therebetween.

When the level of miRNAs in the first subject is greater than the level of miRNAs in second subject by an amount equivalent to less than 1-fold, the calculation indicates an increased risk of failing minimization of IST dosage in a subject under IST treatment. The calculated increase that is less than 1-fold may be an increase that is equivalent to at most about 0.9-, 0.8-, 0.7-, 0.6-, 0.5-, 0.4-, 0.3-, 0.2-, or 0.1-fold, or less.

Accordingly, in the present embodiment, fold changes or equivalents thereof for the miRNA marker are normalized to the spiked-in reference miRNAs.

Detecting Acute Transplant Rejection

In one embodiment, the invention includes a method of detecting acute rejection in a subject having received an organ transplant. The method comprises the steps of detecting a level of expression of miRNA indicative of acute rejection in a test sample from the subject, wherein the miRNA is at least one selected from hsa-miR-125b-5p, hsa-miR-100-5p, hsa-miR-483-5p, hsa-miR-885-5p, hsa-miR-122-5p, hsa-miR-99a-5p, hsa-miR-30a-5p, hsa-miR-497-5p, hsa-miR-194-5p, hsa-miR-34a-5p, hsa-miR-192-5p, hsa-miR-215, hsa-miR-375, hsa-miR-193a-5p, hsa-miR-483-5p, hsa-miR-505-3p, hsa-miR-378a-3p, hsa-miR-193b-3p, hsa-miR-874, hsa-miR-365a-3p, hsa-miR-152, hsa-miR-148a-3p and hsa-miR-29a-5p or any combination thereof. Then comparing the level of expression of the miRNA in the test sample to the level of miRNA in a control sample, wherein an increase between the amount of the miRNA in the test sample relative to the control sample indicates that the subject has acute cellular rejection (ACR). Furthermore, when acute transplant rejection is indicated, treatment for the rejection is recommended.

The invention is based, in part, on the observation that increased expression of certain miRNAs comprising hsa-miR-125b-5p, hsa-miR-100-5p, hsa-miR-483-5p, hsa-miR-885-5p, hsa-miR-122-5p, hsa-miR-99a-5p, hsa-miR-30a-5p, hsa-miR-497-5p, hsa-miR-194-5p, hsa-miR-34a-5p, hsa-miR-192-5p, hsa-miR-215, hsa-miR-375, hsa-miR-193a-5p, hsa-miR-483-5p, hsa-miR-505-3p, hsa-miR-378a-3p, hsa-miR-193b-3p, hsa-miR-874, hsa-miR-365a-3p, hsa-miR-152, hsa-miR-148a-3p and hsa-miR-29a-5p, the miRNAs provided in Table 1, hsa-miR-4'790-5p, hsa-miR-3692-3p, hsa-miR-4433b-3p, hsa-miR-6500-3p, hsa-miR-4445-5p, hsa-miR-5194, hsa-miR-4505, hsa-miR-4430, hsa-miR-374c-3p, hsa-miR-4506, hsa-miR-4286, hsa-miR-6816-5p, hsa-miR-758-3p, hsa-miR-4535, hsa-miR-490-3p, hsa-miR-6765-5p, hsa-miR-3197, hsa-miR-12'71-3p, hsa-miR-92a-1-5p, hsa-miR-8054, hsa-miR-455-5p, hsa-miR-7151-3p, hsa-miR-628-3p, hsa-miR-556-5p, hsa-miR-6726-5p, hsa-miR-1179, hsa-miR-3196, hsa-miR-6858-5p, hsa-miR-6778-5p, hsa-miR-4459, hsa-miR-380-5p, hsa-miR-1273e, hsa-let-7b-3p, hsa-miR-4481, hsa-miR-1908-5p, hsa-miR-149-3p, hsa-miR-651-3p and hsa-miR-124-5p (provided in Table 5), is associated with acute rejection and/or can be used to predict acute rejection in a transplant subject. In a particular embodiment, the miRNAs comprise the three biomarkers hsa-miR-125b-5p, hsa-miR-100-5p and hsa-miR-483-5p.

Predicting Minimization of Immunosuppressive Therapy (IST) Dosage.

In one embodiment, the invention includes a method of detecting a subject that has received an organ transplant and is under IST. The method comprises the steps of detecting a level of expression of miRNA indicative of IST in a test sample from the subject, wherein the miRNA is at least one selected from hsa-miR-146b-5p, hsa-miR-424-3p, hsa-miR-125a-5p, hsa-miR-342-3p, hsa-miR-150-5p, hsa-miR-421, hsa-miR-148a-3p, hsa-miR-223-5p, hsa-miR-495-3p, hsa-miR-497-5p, hsa-miR-29a-3p, hsa-miR-30a-5p, hsa-miR-374b-5p, hsa-let-7g-5p, hsa-miR-99a-5p, hsa-miR-18b-5p, hsa-miR-7-1-3p, hsa-miR-181c-5p, hsa-miR-454-3p, hsa-miR-485-3p, hsa-miR-374a-5p, hsa-miR-99b-5p, hsa-miR-192-5p, hsa-miR-191-5p, hsa-miR-21-5p, hsa-miR-24-3p, hsa-miR-27b-3p, hsa-miR-222-3p, hsa-miR-20a-3p and hsa-miR-106b-5p, or any combination thereof. Then comparing the level of expression of the miRNA in the test sample to the level of miRNA in a control sample, wherein an increase between the amount of the miRNA in the test sample relative to the control sample indicates that the subject is likely to fail a reduction in IST dosage. Further when failure of IST minimization is indicated, treatment of the subject is recommended.

The invention is based, in part, on the observation that increased expression of certain miRNAs comprising hsa-miR-146b-5p, hsa-miR-424-3p, hsa-miR-125a-5p, hsa-miR-342-3p, hsa-miR-150-5p, hsa-miR-421, hsa-miR-148a-3p, hsa-miR-223-5p, hsa-miR-495-3p, hsa-miR-497-5p, hsa-miR-29a-3p, hsa-miR-30a-5p, hsa-miR-374b-5p, hsa-let-7g-5p, hsa-miR-99a-5p, hsa-miR-18b-5p, hsa-miR-7-1-3p, hsa-miR-181c-5p, hsa-miR-454-3p, hsa-miR-485-3p, hsa-miR-374a-5p, hsa-miR-99b-5p, hsa-miR-192-5p, hsa-miR-191-5p, hsa-miR-21-5p, hsa-miR-24-3p, hsa-miR-27b-3p, hsa-miR-222-3p, hsa-miR-20a-3p and hsa-miR-106b-5p (listed in Table 2) is associated with a likelihood of failing minimization of IST dosage in a subject. In a particular embodiments, the miRNAs comprise the three biomarker hsa-miR-146b-5p, hsa-miR-424-3p and hsa-miR-125a-5p.

Based on the data described herein, compositions and methods are now available for the rapid and reliable detection of or prediction of acute rejection even without allograft biopsy, as well as the prediction of success or failure of minimizing IST dosage.

The amounts of any combinations of the miRNAs listed herein may be detected according to the methods disclosed herein and compared with a control (baseline level). In one embodiment, a difference in the level of expression of one miRNA indicates that the subject has or is developing acute rejection. However, in alternate embodiments, changes in the amounts of any combination of two, three, four, six, eight, nine or more miRNAs can indicate that the subject has or is developing acute rejection. In this way, the dose of immunosuppression agents can be modified, e.g., increased or decreased or discontinued and/or new agents can be added to the administered treatment regimen. In some embodiments, other treatment modalities can be initiated, such as for example, plasmapheresis.

In certain aspects of the present invention, the level of miRNA expression is determined for one or more miRNA in a sample obtained from a subject. The sample can be a fluid sample such as a blood sample, preferably containing peripheral blood mononuclear cells (PBMCs), a urine sample, preferably containing urinary cells such as epithelial cells, or infiltrating immune cells, a sample of bronchoalveolar lavage fluid, a sample of bile, pleural fluid or peritoneal fluid, or any other fluid secreted or excreted by a normally or abnormally functioning allograft, or any other fluid resulting from exudation or transudation through an allograft or in anatomic proximity to an allograft, or any fluid that is in physiological contact or proximity with the allograft, or any other body fluid in addition to those recited herein should also be considered to be included in the invention.

Any method known to those in the art can be employed for determining the level of miRNA expression. For example, a microarray can be used. Microarrays are known in the art and consist of a surface to which probes that correspond in sequence to gene products (e.g. mRNAs, polypeptides, fragments thereof etc.) can be specifically hybridized or bound to a known position. To detect at least one miRNA of interest, a hybridization sample is formed by contacting the test sample with at least one nucleic acid probe. A preferred probe for detecting miRNA is a labeled nucleic acid probe capable of hybridizing to miRNA. The nucleic acid probe can be, for example, a full-length nucleic acid molecule, or a portion thereof, such as an oligonucleotide of at least 10, 15, or 20 nucleotides in length and sufficient to specifically hybridize under stringent conditions to appropriate miRNA. The hybridization sample is maintained under conditions which are sufficient to allow specific hybridization of the nucleic acid probe to a miRNA target of interest. Specific hybridization can be performed under high stringency conditions or moderate stringency conditions, as appropriate. In a preferred embodiment, the hybridization conditions for specific hybridization are high stringency. Specific hybridization, if present, is then detected using standard methods. If specific hybridization occurs between the nucleic acid probe and a miRNA in the test sample, the sequence that is present in the nucleic acid probe is also present in the miRNA of the subject. More than one nucleic acid probe can also be used. Hybridization intensity data detected by the scanner are automatically acquired and processed by the Affymetrix Microarray Suite (MASS) software. Raw data is normalized to expression levels using a target intensity of 150. An alternate and preferred method to measure miRNA expression profiles of a small number of different genes is by e.g. either classical TaqMan® Gene Expression Assays or TaqMan® Low Density Array—micro fluidic cards (Applied Biosystems). Particularly, this invention preferably utilizes a microRNA qPCR system. Non-limiting examples include commercial kits such as the PrimePCRPathways® commercially available from Bio-rad (Berkley, Calif.), the miRCURY LNA™ Universal RT microRNA PCR commercially available from Exiqon (Denmark), or the Custom RT2 Profiler PCR Arrays commercially available from Qiagen (Netherlands). Another example of method that can be employed for determining the level of miRNA expression is the use of molecular color-coded barcodes and single molecule imaging to detect and count hundreds of unique transcripts in a single reaction such as in the nCounter® system from Nanostring Technology® (Seattle, Wash.). Using this technology, each color-coded barcode is attached to a single target-specific probe corresponding to a gene of interest so that each color-coded barcode represents a single target molecule. Barcodes hybridize directly to the target molecules and can be individually counted without the need for amplification providing very sensitive digital data. After hybridization, the excess probes are removed and the probe/target complexes are aligned and immobilized in the nCounter® Cartridge. The sample Cartridges are placed in the nCounter® Digital Analyzer for data collection and the color codes on the surface of the cartridge are counted and tabulated for each target molecule.

Other technologies contemplated by this invention for profiling microRNAs rely on the use of hydrogel particles such as the Firefly™ microRNA Assay (Firefly BioWorks Inc, Cambridge, Mass. 02139). This assay, based on porous particle, allows target molecules to diffuse and bind in a unique nanoscale three-dimensional scaffold which favors accurate multiplexed miRNAs detection in a variety of biological samples. The present invention particularly contemplates the use of Firefly™ Circulating microRNA Assay for profiling circulating microRNAs biomarkers directly from a sample such as blood, serum or plasma without any prior RNA purification.

The transcriptional state of a sample, particularly miR-NAs, may also be measured by other nucleic acid expression technologies known in the art.

In one embodiment, the miRNAs are detected in a sample from the recipient of an organ transplant. Any method known to those in the art can be employed for determining the level of microRNAs (particularly, the miRNAs provided elsewhere herein in Tables 1-5). miRNA can be isolated from the sample using any method known to those in the art. Non-limiting examples include commercial kits, such as the miRNeasy® commercially available from Qiagen (Netherlands) or the Mini Kit the TRI Reagent® commercially available from Molecular Research Center, Inc. (Cincinnati, Ohio), can be used to isolate RNA.

Generally, the isolated miRNAs may be amplified using methods known in the art. Amplification systems utilizing, for example, PCR or RT-PCR methodologies are known to those skilled in the art. For a general overview of amplification technology, see, for example, Dieffenbach et al., PCR Primer: A Laboratory Manual, Cold Spring Harbor Laboratory Press, New York (1995).

An alternative method for determining the level of microRNAs (particularly, the miRNAs provided elsewhere herein in Tables 1-5) includes the use of molecular beacons and other labeled probes useful in, for example multiplex PCR. In a multiplex PCR assay, the PCR mixture contains primers and probes directed to the selected miRNAs PCR product. Typically, a single fluorochrome is used in the assay. The molecular beacon or probe is detected to determine the level of miRNA. Molecular beacons are described, for example, by Tyagi and Kramer (Nature Biotechnology 14, 303-308, 1996) and by Andrus and Nichols in U.S. Patent Application Publication No. 20040053284.

Another accurate method for profiling miRNA expression can the use of Next Generation Sequencing (NGS) including first, second, third as well as subsequent Next Generations Sequencing technologies. Non limiting examples could be the nanopore or semiconductor technologies (e.g. Oxford Nanopore Technologies, United Kingdom) or the Illumina microRNA-Seq Platform (Luo S., 2012, Methods Mol Biol. 822:183-8).

In some embodiments, upregulation of miRNA level includes increases above a baseline level of 1-, 2-, 3-, 4-, 5-, 6-, 7-, 8-, 9-, 10-, 11-, 12-, 13-, 14-, 15-, 16-, 17-, 18-, 19-, 20-fold, or more and any and all partial integers therebetween; as well as above a baseline level of 0.9-, 0.8-, 0.7-, 0.6-, 0.5-, 0.4-, 0.3-, 0.2-, or 0.1-fold, or less.

In some embodiments, the level of expression is determined using log-transformed miRNA levels. The log transformation or miRNA levels substantially reduce the positive skew in the data. In some embodiments, the level of expression is determined using log-transformed miRNA levels determined by normalizing miRNA levels using a logistic regression model. Logistic regression models are used for prediction of the probability of occurrence of acute rejection by fitting data to a logistic curve. It is a generalized linear model used for binomial regression.

In some embodiments, for interpretation of quantitative nucleic acid expression measurements, a normalizer may be needed to correct expression data for differences in sample input, RNA quality, and RT efficiency between samples. In some embodiments, to accurately assess whether increased miRNA is significant, the miRNA expression can be normalized to accurately compare levels of expression between samples, e.g., it is a baseline level against which expression is compared. In quantitative assays, such as for example, quantitative real-time Reverse Transcriptase-PCR (qRT-PCR) normalization can be performed using spiked-in markers as references against the expression level of a miRNA under investigation. Normalization includes rendering the measurements of different arrays or PCR or in particular RT-PCR experiments comparable by reducing or removing the technical variability. Within these experiments there exists a multiplicity of sources capable of falsifying the measurements. Possible technical sources of interference are: different efficiency in reverse transcription, labeling or hybridization reactions, as well as problems with the arrays, batch effects in reagents, or lab-specific conditions. By normalization a more robust detection of miRNA expression can occur.

Typically, miRNA normalization involves use of spiked-in markers that have known fractional cycle number or crossing point. These are utilized as a reference, internal control or reference values in the quantification of miRNA expression. A spiked-in marker exhibits minimum change of expression and transcription across different miRNA samples and thus serves as a control, or reference, for the measurement of variable miRNA activities across different samples. Spiked-in markers can be, but are not limited to, UniSp2 and UniSp4 (Exiqon, Denmark).

Receiver Operating Characteristic (ROC) curves can be generated for individual miRNA levels and a linear combination of miRNA levels to determine the cutoff points that yielded the highest combined sensitivity and specificity for detecting ACR or anticipating ACR as well as detecting the likelihood of successful minimization of IST.

This involves measuring the miRNA levels alone, all together, or in any combination for the following hsa-miR-125b-5p, hsa-miR-100-5p, hsa-miR-483-5p, hsa-miR-885-5p, hsa-miR-122-5p, hsa-miR-99a-5p, hsa-miR-30a-5p, hsa-miR-497-5p, hsa-miR-194-5p, hsa-miR-34a-5p, hsa-miR-192-5p, hsa-miR-215, hsa-miR-375, hsa-miR-193a-5p, hsa-miR-483-5p, hsa-miR-505-3p, hsa-miR-378a-3p, hsa-miR-193b-3p, hsa-miR-874, hsa-miR-365a-3p, hsa-miR-152, hsa-miR-148a-3p and hsa-miR-29a-5p; and/or hsa-miR-146b-5p, hsa-miR-424-3p, hsa-miR-125a-5p, hsa-miR-342-3p, hsa-miR-150-5p, hsa-miR-421, hsa-miR-148a-3p, hsa-miR-223-5p, hsa-miR-495-3p, hsa-miR-497-5p, hsa-miR-29a-3p, hsa-miR-30a-5p, hsa-miR-374b-5p, hsa-let-7g-5p, hsa-miR-99a-5p, hsa-miR-18b-5p, hsa-miR-7-1-3p, hsa-miR-181c-5p, hsa-miR-454-3p, hsa-miR-485-3p, hsa-miR-374a-5p, hsa-miR-99b-5p, hsa-miR-192-5p, hsa-miR-191-5p, hsa-miR-21-5p, hsa-miR-24-3p, hsa-miR-27b-3p, hsa-miR-222-3p, hsa-miR-20a-3p and hsa-miR-106b-5p. These combinations are then weighted based on increased expression. These statistical analyses with different biomarkers are described in Zhang et al., 2005, Biostatistics Working Paper Series. Other statistical analysis methods for quantifying biomarkers known in the art can be used as well.

Compositions

The invention includes a set of preferred probes or primers, either labeled (e.g., fluorescer, quencher, etc.) or unlabeled, that are useful for the detection of at least three miRNAs selected from the group consisting of hsa-miR-125b-5p, hsa-miR-100-5p, hsa-miR-483-5p, hsa-miR-885-5p, hsa-miR-122-5p, hsa-miR-99a-5p, hsa-miR-30a-5p, hsa-miR-497-5p, hsa-miR-194-5p, hsa-miR-34a-5p, hsa-miR-192-5p, hsa-miR-215, hsa-miR-375, hsa-miR-193a-5p, hsa-miR-483-5p, hsa-miR-505-3p, hsa-miR-378a-3p, hsa-miR-193b-3p, hsa-miR-874, hsa-miR-365a-3p, hsa-miR-152, hsa-miR-148a-3p, hsa-miR-29a-5p (Table1), hsa-miR-4790-5p, hsa-miR-3692-3p, hsa-miR-4433b-3p, hsa-miR-6500-3p, hsa-miR-4445-5p, hsa-miR-5194, hsa-miR-4505, hsa-miR-4430, hsa-miR-374c-3p, hsa-miR-4506, hsa-miR-4286, hsa-miR-6816-5p, hsa-miR-758-3p, hsa-miR-4535, hsa-miR-490-3p, hsa-miR-6765-5p, hsa-miR-3197, hsa-miR-1271-3p, hsa-miR-92a-1-5p, hsa-miR-8054, hsa-miR-455-5p, hsa-miR-7151-3p, hsa-miR-628-3p, hsa-miR-556-5p, hsa-miR-6726-5p, hsa-miR-1179, hsa-miR-3196, hsa-miR-6858-5p, hsa-miR-6778-5p, hsa-miR-4459, hsa-miR-380-5p, hsa-miR-1273e, hsa-let-7b-3p, hsa-miR-4481, hsa-miR-1908-5p, hsa-miR-149-3p, hsa-miR-651-3p and hsa-miR-124-5p (Table 5); and/or hsa-miR-146b-5p, hsa-miR-424-3p, hsa-miR-125a-5p, hsa-miR-342-3p, hsa-miR-150-5p, hsa-miR-421, hsa-miR-148a-3p, hsa-miR-223-5p, hsa-miR-495-3p, hsa-miR-497-5p, hsa-miR-29a-3p, hsa-miR-30a-5p, hsa-miR-374b-5p, hsa-let-7g-5p, hsa-miR-99a-5p, hsa-miR-18b-5p, hsa-miR-7-1-3p, hsa-miR-181c-5p, hsa-miR-454-3p, hsa-miR-485-3p, hsa-miR-374a-5p, hsa-miR-99b-5p, hsa-miR-192-5p, hsa-miR-191-5p, hsa-miR-21-5p, hsa-miR-24-3p, hsa-miR-27b-3p, hsa-miR-222-3p, hsa-miR-20a-3p and hsa-miR-106b-5p (Table 2). Particularly preferred probe sets comprise probes that are capable of detecting the three biomarkers hsa-miR-483-5p, hsa-miR-125b-5p and hsa-miR-100-5p for the diagnosis or prediction of ACR; and the three biomarkers hsa-miR-146b-5p, hsa-miR-424-3p and hsa-miR-125a-5p for the diagnosis of tolerance for minimization of IST.

Kits

In certain embodiments, kits are provided. Commercially available kits for use in these methods are, in view of this specification, known to those of skill in the art. In general, kits will comprise a detection reagent that is suitable for detecting the presence of a polypeptide or nucleic acid, or mRNA of interest.

In another embodiment, there is a panel of probe sets. Preferred probe sets are designed to detect expression of one or more miRNAs and provide information about the rejection of a graft and/or the minimization of IST. Probe sets are particularly useful because they are smaller and cheaper than probe sets that are intended to detect as many miRNAs as possible in a particular genome. The probe sets are targeted at the detection of miRNAs that are informative about acute rejection or tolerance for IST minimization. Probe sets may also comprise a large or small number of probes that detect miRNAs that are not informative about transplant rejection or minimization of IST. Such probes are useful as controls and for normalization (e.g., spiked-in markers). Probe sets may be a dry mixture or a mixture in solution. In some embodiments, probe sets can be affixed to a solid substrate to form an array of probes. It is anticipated that probe sets may also be useful for multiplex PCR. The probes may be nucleic acids (e.g., DNA, RNA, chemically modified forms of DNA and RNA), LNAs (Locked nucleic acids), or PNAs (Peptide nucleic acids), or any other polymeric compound capable of specifically interacting with the desired nucleic acid sequences.

It is contemplated that kits may be designed for isolating and/or detecting miRNA in essentially any sample (e.g., urine, blood, etc.), and a wide variety of reagents and methods are, in view of this specification, known in the art.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in the experiments disclosed herein are now described.

Materials and Methods
Clinical Trial Studies.

Data from three clinical trial studies from The National Institutes of Health (NIH) were used herein. The Immune Tolerance Network A-WISH study (ITN study: ITN030, available at www.clinicaltrials.gov/ct2/show/record/NCT00135694), Clinical Trials in Organ Transplantation (CTOT-03, available at www.clinicaltrials.gov/ct2/show/NCT00531921?term=CTOT-03&rank=1), and Adult to Adult Liver Living Donors Liver Transplantation (A2ALL, available at www.clinicaltrials.gov/ct2/show/NCT02073435?term=A2ALL&rank=2).

Inclusion and Exclusion Criteria.

Study subjects were required to be adult recipients transplanted for non-immune liver disease, including subjects treated for HCV infection prior to transplantation who remain SVR at the time of clinically indicated liver biopsy. Subjects should receive tacrolimus-based immunosuppression. Overall, the CTOT-03 and -04 protocols demonstrated a >95% consent rate among subjects approached for entry into observational study involving blood collections.

miRNA Profiles.

RNA was extracted from the subject's serum followed by miRNA profiling and analysis. miRNA profiling was done via miRCURY LNA™ Universal RT microRNA PCR panels (Exiqon, Denmark). Serum input is held constant to assure the same eluted volume of nucleic acids is used in each reverse transcription reaction. Spike-in assays controlled the efficiencies of extraction, reverse transcription and real-time PCR. Standard miRNA PCR array was used with spiked-in markers that have known Cq (fractional cycle number or crossing point) value to allow quantitative measurements of signature miRNAs.

Expression Data Normalization

After Inter-Plate-Calibration (IPC), individual measurements that were beyond cycle threshold were replaced with the highest Cq value output from the run to allow their inclusion in subsequent processing, as the measurements were below detection limits rather than true missing value. These values were subtracted from 36 to provide a relative expression value (on log 2-scale) with zero set at approximately the reliable quantification limit for qPCR-based assays. To normalize for technical processing variations, for each sample, the average of the deviation from the study population mean for the UniSp2 and UniSp4 (Exiqon, Denmark) exogenous spiked miRNA was subtracted from the relative expression values for each miRNA within the respective sample. From analysis of population variance vs. mean plot for the normalized miRNA expression values, the limit of detection (LOD) was estimated to be above 0, but could be extended to be above −2, with the limitation of population standard deviation being below 2.5. Based on this LOD, miRNA that had a relative expression value below −2 were adjusted to −3. miRNA that had a population mean below −2 or population standard deviation above 2.5 were flagged as inappropriate for continuous variable analysis. If the miRNA had signal above −2 for at least two samples for ACR=Yes and ACR=No subgroups, then the miRNA was considered for categorical analysis after dichotomization of values to '1' if relative expression was above −2 or '0' otherwise. miRNA that were not considered for continuous variable or categorical analyses were not included in subsequent statistical analyses.

Statistical Analysis

Normalized miRNA expression values were imported into Array Studio software (www.omicsoft.com) for additional data QC and single variable analysis. Outliers implicated by both Principal Components Analysis (PCA) clustering and MAD scores were excluded. Serum samples collected during biopsy-proven ACR and no-rejection episodes were randomly assigned to discovery (14 ACR and 37 non-ACR samples), and replication (13 ACR and 40 non-ACR samples) sets. The associations between ACR status and individual miRNA expression levels were tested using general linear model, adjusting for the potential cofounder time since transplantation. False discovery rate (FDR) was applied for multiple testing correction.

Logistic regression analysis was used to identify parsimonious subsets of ACR-associated serum miRNAs that discriminated ACR from non-ACR episodes. Models with up to 6-terms were built with hierarchical forward with switching as the variable selection method. From those models in which each predictor was significant at P<0.1, provisionally selection was based on the miRNA with the greatest log-likelihood and greatest area under the receiver-operating-characteristic (ROC) curve as the best-fitting model. The regression estimates from this model defined a diagnostic signature, and area under the curve (AUC), sensitivity, and specificity were used to evaluate the ability of this signature to discriminate ACR from non-ACR episodes.

To validate the miRNA diagnostic signature obtained above, the regression coefficients for the miRNAs included in the diagnostic signature obtained from ITN samples were used to calculate a composite score to summarize the expression values of these miRNAs for each sample in the replication datasets (samples obtained from CTOT-03 study and samples collected from non-randomized subjects participating in ITN trial). The composite scores were then used in a logistic regression model. % correct classification, AUC, sensitivity and specificity were calculated for these two replication datasets.

To investigate the predictive value of the diagnostic signature obtained, LOESS (locally estimated scatterplot smoothing) curves with corresponding 95% confidence intervals (CI) were obtained for the retrospective trajectories of the diagnostic signature, looking backwards from the time of biopsy for ACR and non-ACR episodes.

To identify the tolerance biomarkers, 10 serum samples from those subjects who were tolerant at the 25% immunosuppression dose were compared with 11 serum samples from subjects who failed at the 25% IST dose. The associations between fail-tolerance status and individual miRNA expression levels at the 25% IST dose were tested using general linear model, adjusting for the potential cofounder time since transplantation. False discovery rate (FDR) was applied for multiple testing correction. Logistic regression analysis was used to build model consisting of three IST-tolerance-associated serum miRNAs that passed multiple-testing correction. The regression estimates from this model defined an IST minimization signature, and area under the curve (AUC), sensitivity, and specificity were used to evaluate the ability of this signature to discriminate subjects who tolerated from subjects who failed 25% immunosuppression dose at various immunosuppression minimization dosages.

All statistical analyses were performed in Array Studio software (www.omicsoft.com), NCSS version 8.0.14 (www.ncss.com), and R (cran.r-project.org).

Power and Sample Size.

Power and sample size calculations were performed assuming the use of general linear model. Estimates from the ITN study were used for power calculation because of its larger sample size and more stable variance estimates. Based on the observed within-group variances of the 3-miRNA ACR-Dx biomarker model prediction score and the proportion of subjects expected to have biopsy proven rejection, 75 subjects (25 rejection cases and 50 control non-rejection subjects) were estimated in power analyses to be needed to have 90% power at alpha=0.00001 to observe a significant difference in mean at the same magnitude as was observed in the ITN study, or alpha=0.001 to observe significant difference in mean at 75% level as what observed in the ITN study.

Tables

Table 1: List of miRNAs associated with ACR diagnosis with a 2-stage study.
Table 2: List of significant miRNAs (P<0.01) between failed and tolerant samples at 25% immunosuppression minimization.
Table 3: List of miRNAs associated with ACR diagnosis detected in the follow up study including 19 ACR and 16 non-ACR samples.
Table 4: List of top ACR-associated miRNAs identified using Exiqon human miRNA panel and confirmed with Qiagen Human miRNome miRNA PCR Array
Table 5: List of top ACR-associated miRNAs (nominal p<0.15) identified using Qiagen Human miRNome miRNA PCR Array.
Table 6: List of the miRNAs biomarkers and their related target sequence selected for ACR prediction and/or IST minimization tolerance.
Table 7: Sequence identifiers for the miRNAs biomarkers and their related target sequence selected for ACR prediction and/or IST minimization tolerance.

The results of the experiments are now described in the following examples.

Example 1: Identification of Serum miRNA Signatures for the Detection and Prediction of Acute Cellular Rejection (ACR)

The results presented herein demonstrate that the miRNA profiles obtained at the time of clinically indicated biopsy are diagnostic of biopsy-confirmed acute rejection at any time after transplantation.

miRNA profiling was performed on 233 serum samples from 42 clinical trial participants from the National Institutes of Health Immune Tolerance in Transplantation-30 (ITN-30) study. This included 33 subjects randomized to immunosuppression withdrawal and 9 subjects randomized to maintenance, using the miRCURY LNA™ Universal RT microRNA PCR v3 panel (Exiqon, Denmark). The primary aims of this study were: 1) to identify serum miRNA signatures for diagnosis of acute cellular rejection (ACR) events; 2) to identify serum miRNA signatures for prediction of ACR events; 3) to identify serum miRNA signatures to differentiate subjects who fail immunosuppression withdrawal from subjects who develop tolerance; and 4) to identify miRNA markers that are associated with immunosuppression doses and trough levels. The Exiqon miRNA panel included unique 752 miRNA assays of which 240 were above the lower limit of reliable quantification in a sufficient proportion of samples to allow for meaningful statistical analysis. A comparison of serum samples from biopsy proven rejection and serum samples without biopsy proven rejection in a two-stage study design (a discovery phase consisting of 14 ACR samples and 37 non-ACR samples; with a replication phase consisting of 13 ACR samples and 40 non-ACR samples) was conducted. From the miRNAs that were nominally significant (P<0.05) in the discovery phase 11 of 26 were confirmed at P<0.05 in the replication phase. In the combined dataset, 15 miRNAs were significantly associated with ACR diagnosis after multiple testing correction (FDR adjusted P<0.05) (Table 1). These 15 miRNA include all of the 11 miRNA replicated between discovery and replication phases. To build a multiple marker panel/signature that may better differentiate ACR from non-ACR, the aforementioned 15 significant miRNAs and time since randomization were used as inputs in logistic regression modeling for forward variable selection. Three miRNAs, hsa-miR-125b, hsa-miR-100 and hsa-miR-483, remained in the final parsimonious model. The logistic regression model composed of these three miRNAs (herein referred to as the 3-miRNA serum ACR diagnosis signature) provides ability to differentiate ACR from non-ACR with an area under the curve (AUC) of 0.898, 92.6% sensitivity and 84.2% specificity (P=0.0001) (FIG. 1).

Figure 2:
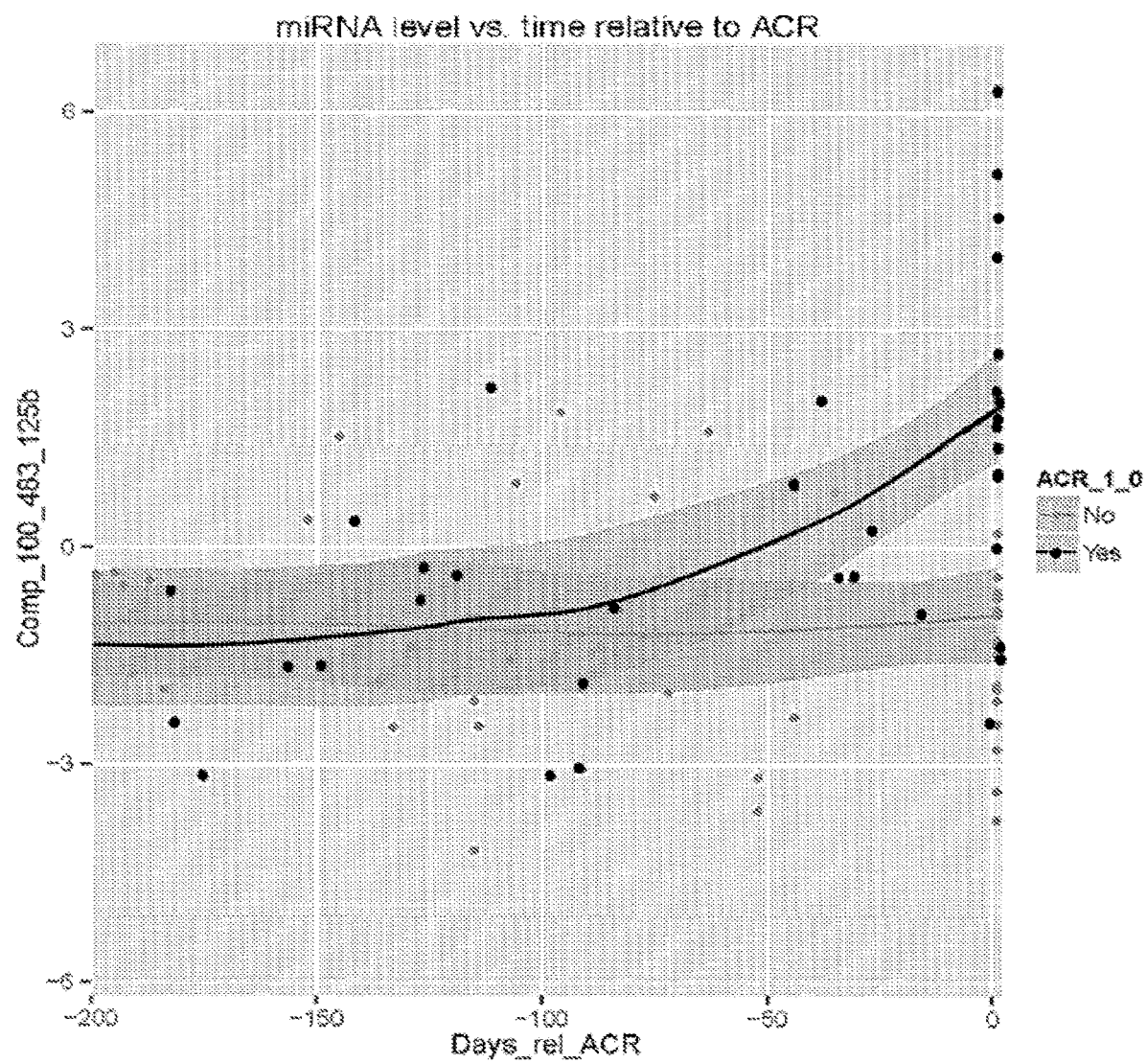
FIG. 2 is a graph that depicts the LOESS smoothing (non-parametric regression methodology) plot of the composite scores of 3-miRNA ACR signature (hsa-miR-125b, hsa-miR-100 and hsa-miR-483) up to the day of biopsy diagnosed rejection. The signature prediction of an ACR is labeled "Yes" and a non-ACR is labeled "No".

Using the aforementioned 3-miRNA serum ACR diagnosis signature as a prediction signature for ACR in liver transplantation, the invention herein assessed the trajectory towards rejection as well as the diagnosis and prognosis for minimization of the immunosuppressive therapy (IST) dose. Specifically, the possibility of using the 3-miRNA serum ACR diagnosis signature to predict ACR events was explored before the onset of rejection. As shown in the LOESS plot (FIG. 2), the miRNA signature model score was elevated before the occurrence of ACR (at day 0) whereas the level of the signature model score remained un-elevatein non-ACR group, with the 95% confidence band of ACR separated from that of non-ACR 40 days before ACR events.
d

TABLE 1

Table 1 lists the identified miRNAs associated with ACR diagnosis with a 2-stage study. The discovery phase with 14 ACR samples and 37 non-ACR samples identified 26 miRNAs with P < 0.05. In replication phase with independent 13 ACR samples and 40 non-ACR samples, 11 of the 26 significant miRNAs were replicated at P < 0.05. 25/26 miRNA trended in the same direction of association, with only one miRNA showing the opposite direction of association, indicating consistency in both study phases. In the combined dataset, 15 miRNAs were found to be associated with ACR diagnosis after multiple test correction (FDR P < 0.05). The 3 miRNAs utilized to generate the multi-marker signature are marked by the symbol **. The Benjamini-Hochberg procedure (BH step-up procedure) controls the false discovery rate (at level alpha) termed FDR-BH.

| ID | Discovery Phase | | | Replication Phase | | | Combined (Discovery + Replication) | | |
|---|---|---|---|---|---|---|---|---|---|
|  | Fold-change | RawP Value | FDR-BH | Fold-change | RawP Value | FDR-BH | Fold-change | RawP Value | FDR-BH |
| hsa-miR-483-5-p ** | 2.943 | 0.0009 | 0.0325 | 3.1558 | 0.0007 | 0.0174 | 3.0297 | 1.5698E−06 | 0.0002 |
| hsa-miR-885-5p | 5.0249 | 9.06E−05 | 0.0178 | 3.6042 | 5.40E−03 | 0.0341 | 4.2977 | 1.76E−06 | 0.0002 |
| hsa-miR•125b-5p ** | 2.6807 | 0.0005 | 0.0308 | 2.5825 | 0.004 | 0.0341 | 2.6241 | 6.5752E−06 | 0.0005 |
| hsa-miR-122-5p | 4.3631 | 0.0001 | 0.0178 | 2.8355 | 0.0185 | 0.0678 | 3.5258 | 0.000013505 | 0.0008 |
| hsa-miR-99a-5p | 3.0213 | 0.0007 | 0.0308 | 2.1309 | 0.0173 | 0.0678 | 2.5397 | 0.000032828 | 0.0014 |
| hsa-miR-30a-5p | 2.2002 | 0.0048 | 0.1181 | 2.0876 | 0.0025 | 0.033 | 2.1308 | 0.00003452 | 0.0014 |
| hsa-miR-100-5p ** | 3.3132 | 0.0006 | 0.0308 | 2.3914 | 0.0231 | 0.0678 | 2.7997 | 0.000060205 | 0.0021 |
| hsa-miR-497-5p | 1.8997 | 0.0117 | 0.2198 | 1.7814 | 0.0066 | 0.0341 | 1.8416 | 0.0002 | 0.0053 |
| hsa-miR-194-5p | 2.5048 | 0.0026 | 0.0702 | 1.9288 | 0.0432 | 0.102 | 2.2043 | 0.0003 | 0.0083 |
| hsa-miR-34a-5p | 2.2139 | 0.0075 | 0.1517 | 2.224 | 0.0235 | 0.0678 | 2.2307 | 0.0004 | 0.0102 |
| hsa-miR-192-5p | 2.6448 | 0.0008 | 0.0308 | 1.7659 | 0.1278 | 0.2215 | 2.1752 | 0.0008 | 0.0178 |
| hsa-miR-215 | 2.8864 | 0.0055 | 0.1218 | 2.1567 | 0.0603 | 0.1206 | 2.497 | 0.0009 | 0.0178 |
| hsa-miR-375 | 2.9171 | 0.0228 | 0.2648 | 2.5796 | 0.0324 | 0.0842 | 2.7311 | 0.0015 | 0.0282 |
| hsa-miR-193a-5p | 2.3295 | 0.0141 | 0.2299 | 1.8149 | 0.0503 | 0.1089 | 2.06 | 0.0016 | 0.0282 |
| hsa-miR-483-3p | 3.5557 | 0.0024 | 0.0702 | 1.7078 | 0.2362 | 0.2791 | 2.4712 | 0.0029 | 0.0474 |
| hsa-miR-505-3p | 2.0367 | 0.0161 | 0.2452 | 1.4995 | 0.1608 | 0.2288 | 1.7504 | 0.0058 | 0.084 |
| hsa-miR-378a-3p | 1.6826 | 0.0471 | 0.4419 | 1.5235 | 0.1007 | 0.1869 | 1.6069 | 0.0085 | 0.0992 |
| hsa-miR-193b-3p | 3.0741 | 0.0192 | 0.2537 | 2.0751 | 0.176 | 0.2288 | 2.5326 | 0.0088 | 0.0992 |
| hsa-miR-874 | 2.4234 | 0.0243 | 0.2648 | 1.5514 | 0.1644 | 0.2288 | 1.9256 | 0.0089 | 0.0992 |
| hsa-miR-365a-3p | 2.1253 | 0.0396 | 0.3866 | 1.6169 | 0.1482 | 0.2288 | 18571 | 0.0108 | 0.1114 |
| hsa-miR-152 | 1.8159 | 0.025 | 0.2648 | 1.3642 | 0.2 | 0.2477 | 1.5698 | 0.011 | 0.1114 |
| hsa-miR-148a-3p | 1.9598 | 0.0385 | 0.3866 | 1.5212 | 0.1707 | 0.2288 | 1.7321 | 0.0124 | 0.1206 |
| hsa-miR-29a-5p | 2.4134 | 0.0138 | 0.2299 | 1.257 | 0.5467 | 0.5685 | 1.7262 | 0.0431 | 0.3758 |
| hsa-miR-210 | 1.8276 | 0.0217 | 0.2648 | 1.2748 | 0.5034 | 0.5453 | 1.529 | 0.0542 | 0.4412 |
| hsa-miR-33b-5p | 2.2862 | 0.0175 | 0.2517 | 1.114 | 0.7815 | 0.7815 | 1.6104 | 0.0652 | 0.4968 |
| hsa-miR-432-5p | −2.288 | 0.0198 | 0.2537 | 1.4459 | 0.3348 | 0.3785 | −1.2684 | 0.3639 | 0.9992 |

** miRNA utilized to generate multi-marker signature (3-miRNA ACR-Dx)

Example 2: Identification of Serum miRNA Signatures for the Prediction of Immunosuppression Minimization Tolerance These experiments were designed to identify additional clinically relevant biomarkers for immunosuppression minimization that are predictive of which subjects will be able to tolerate lower doses of medication without inducing rejection. To identify each tolerance biomarkers, 10 serum samples from those subjects who were tolerant at the 25% immunosuppression dose (also meant by that a decrease of the initial IST dose by 75%) were compared with 11 serum samples from subjects who failed at the 25% IST dose (these serum samples were taken 58 days on average before rejection occurred). The 25% IST dose was used as the basis for this comparison because a large proportion of subjects (40% of all participants) failed at this stage, and this may represent where major changes occur in serum miRNAs that best differentiate patients who may tolerate or fail at lower IST doses As shown in Table 2, the level of 30 miRNAs were found to be significantly different at P<0.01 between samples taken from those who eventually failed at the 25% IST dose and those who were tolerant at the 25% IST dose. Three miRNAs were still significant after multiple testing correction (FDR P<0.05). It is noted that the serum miRNA biomarkers for ACR diagnosis are not on the higher significant list for biomarkers for tolerance, indicating potential biological differences in the physiological states of rejection vs. tolerance.

Figure 3:
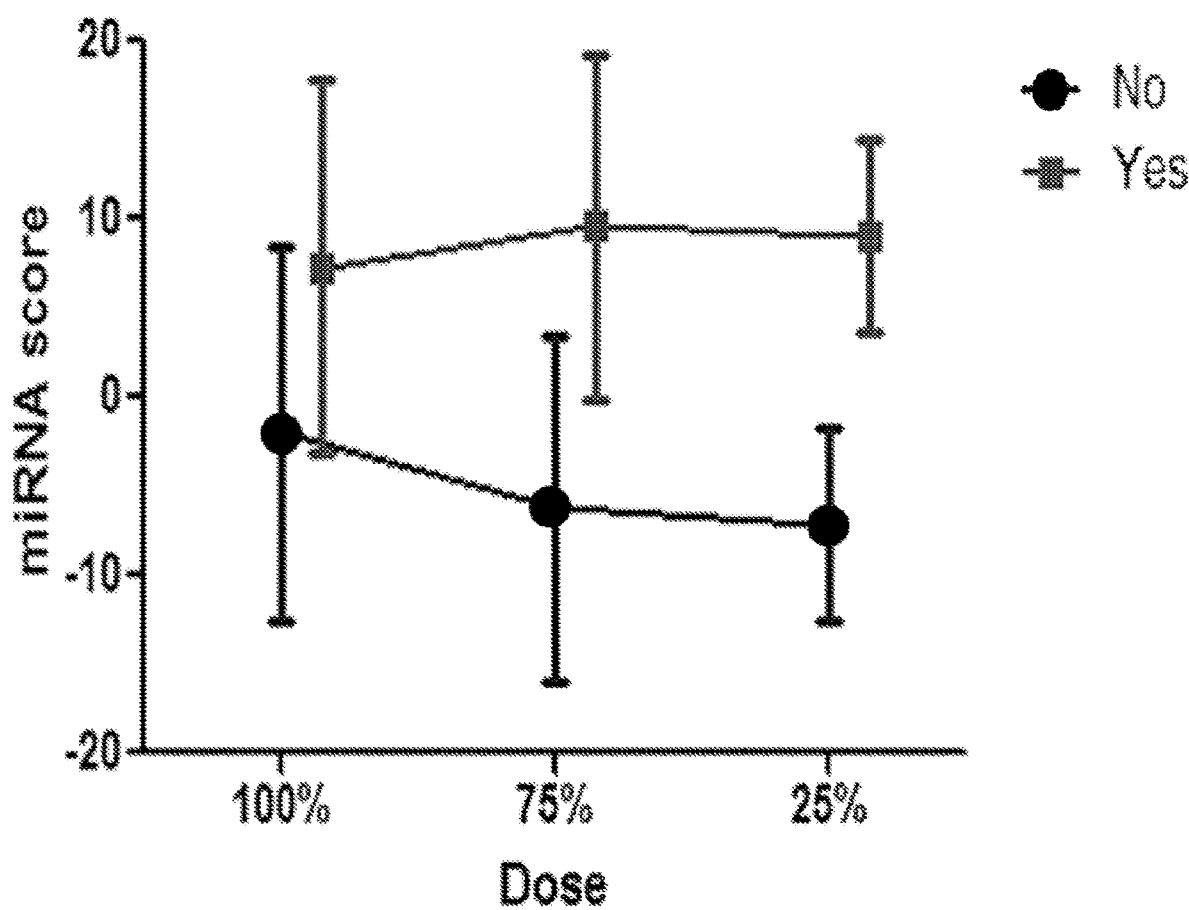
FIG. 3 is a graph illustrating the composite scores (least square means±standard deviation, SD) of 3-miRNA tolerant signature at various doses during immunosuppression minimization between those who failed 25% dose (label="Yes") and those who were tolerant at 25% dose (label="No").

To test whether the identified tolerance related miRNA biomarkers have predictive value, a composite score model was constructed including the three miRNAs that passed the FDR<0.05 significance threshold (hsa-miR-146b, hsa-miR-424 and hsa-miR-125a) for tolerance association at the 25% IST dose. Composite scores computed based on the expression levels of the 3 miRNAs at the 75% IST dose or at randomization (100% IST dose) were used to test whether those subjects who were tolerant at the 25% IST dose could be differentiated from those who failed at the 25% IST dose. As shown in FIG. 3, the 3-miRNA tolerance signature model at either the 75% (P=0.02) or 100% (P=0.06) IST dose can differentiate those subject who eventually failed at the 25% IST dose from those subject who eventually became tolerance at the 25% IST dose. The scores from the 3-miRNA tolerance signature model at the 75% IST dose was estimated to have AUC=0.877, sensitivity=0.82, specificity=0.90 to predict who will fail or become tolerant at the 25% IST dose. The results demonstrate the ability to greatly improve the IST minimization process by predicting which patients may go on to exhibit a 25% IST dose early-on during the minimization process when the failure rate is minimal (93% subjects estimated to be able to tolerant a 75% IST dose, based on our ITN data).

TABLE 2

Table 2 Lists 30 serum miRNAs that were significant at P < 0.01 for the comparison of failed and tolerant samples at 25% immunosuppression minimization.

| ID | Failed.vs.Tolerant FoldChange | Failed.vs.Tolerant Raw P-Value | Failed.vs.Tolerant FDR P-Value |
|---|---|---|---|
| hsa-miR-146b-5p | 3.3138 | 0.0004 | 0.044 |
| hsa-miR-424-3p | 5.9117 | 0.0004 | 0.044 |
| hsa-miR-125a-5p | 3.6992 | 0.0006 | 0.044 |
| hsa-miR-342-3p | 2.2354 | 0.0019 | 0.0719 |
| hsa-miR-150-5p | 2.3795 | 0.002 | 0.0719 |
| hsa-miR-421 | 6.7364 | 0.0021 | 0.0719 |
| hsa-miR-148a-3p | 3.133 | 0.0025 | 0.0719 |
| hsa-miR-223-5p | 4.4363 | 0.0025 | 0.0719 |
| hsa-miR-495-3p | 2.8986 | 0.0036 | 0.0719 |
| hsa-miR-497-5p | 2.6304 | 0.0039 | 0.0719 |
| hsa-miR-29a-3p | 2.5658 | 0.0039 | 0.0719 |
| hsa-miR-30a-5p | 2.5706 | 0.0043 | 0.0719 |
| hsa-miR-374b-5p | 4.4668 | 0.0047 | 0.0719 |
| hsa-let-7g-5p | 3.0967 | 0.0048 | 0.0719 |
| hsa-miR-99a-5p | 2.4666 | 0.0057 | 0.0719 |
| hsa-miR-18b-5p | 2.9925 | 0.0063 | 0.0719 |
| hsa-miR-7-1-3p | 4.4785 | 0.0063 | 0.0719 |
| hsa-miR-181c-5p | 3.3391 | 0.0065 | 0.0719 |
| hsa-miR-454-3p | 3.0594 | 0.0072 | 0.0719 |
| hsa-miR-485-3p | 1.8711 | 0.0073 | 0.0719 |
| hsa-miR-374a-5p | 3.8964 | 0.0075 | 0.0719 |
| hsa-miR-99b-5p | 2.397 | 0.0079 | 0.0719 |
| hsa-miR-192-5p | 2.606 | 0.0081 | 0.0719 |
| hsa-miR-191-5p | 3.2862 | 0.0081 | 0.0719 |
| hsa-miR-21-5p | 2.1481 | 0.0083 | 0.0719 |
| hsa-miR-24-3p | 2.7691 | 0.0083 | 0.0719 |
| hsa-miR-27b-3p | 2.7774 | 0.0084 | 0.0719 |
| hsa-miR-222-3p | 2.2814 | 0.0086 | 0.0719 |
| hsa-miR-20a-3p | 4.298 | 0.0087 | 0.0719 |
| hsa-miR-106b-5p | 2.8124 | 0.0094 | 0.0719 |

Example 3: Replication of miRNA Sera Signatures for Detection and Prediction of Acute Cellular Rejection (ACR)

To initially replicate the list of 23 ACR-associated miRNAs as well as the 3-miRNA signature identified previously for ACR diagnosis signature (Phase I study, presented previously in Example 1), miRNA profiling of serum samples from two independent studies were subsequently analyzed via the 752 miRCURY LNA™ Universal RT microRNA PCR v3 panels from Exiqon (Denmark). The first study comprised 15 ACR and 5 non-ACR serum samples from the ITN participants who were not randomized to IST withdrawal or maintenance. The second study comprised 4 ACR and 11 non-ACR samples from the NIH-CTOT03 prospective study. After excluding miRNAs that failed standard quality control (QC) measures, 20 of the 23 ACR-associated miRNAs were included in logistic regression modelling to test their association with ACR. As shown in Table 3, all 20 miRNAs were replicated in this follow-up study.

Figure 4:
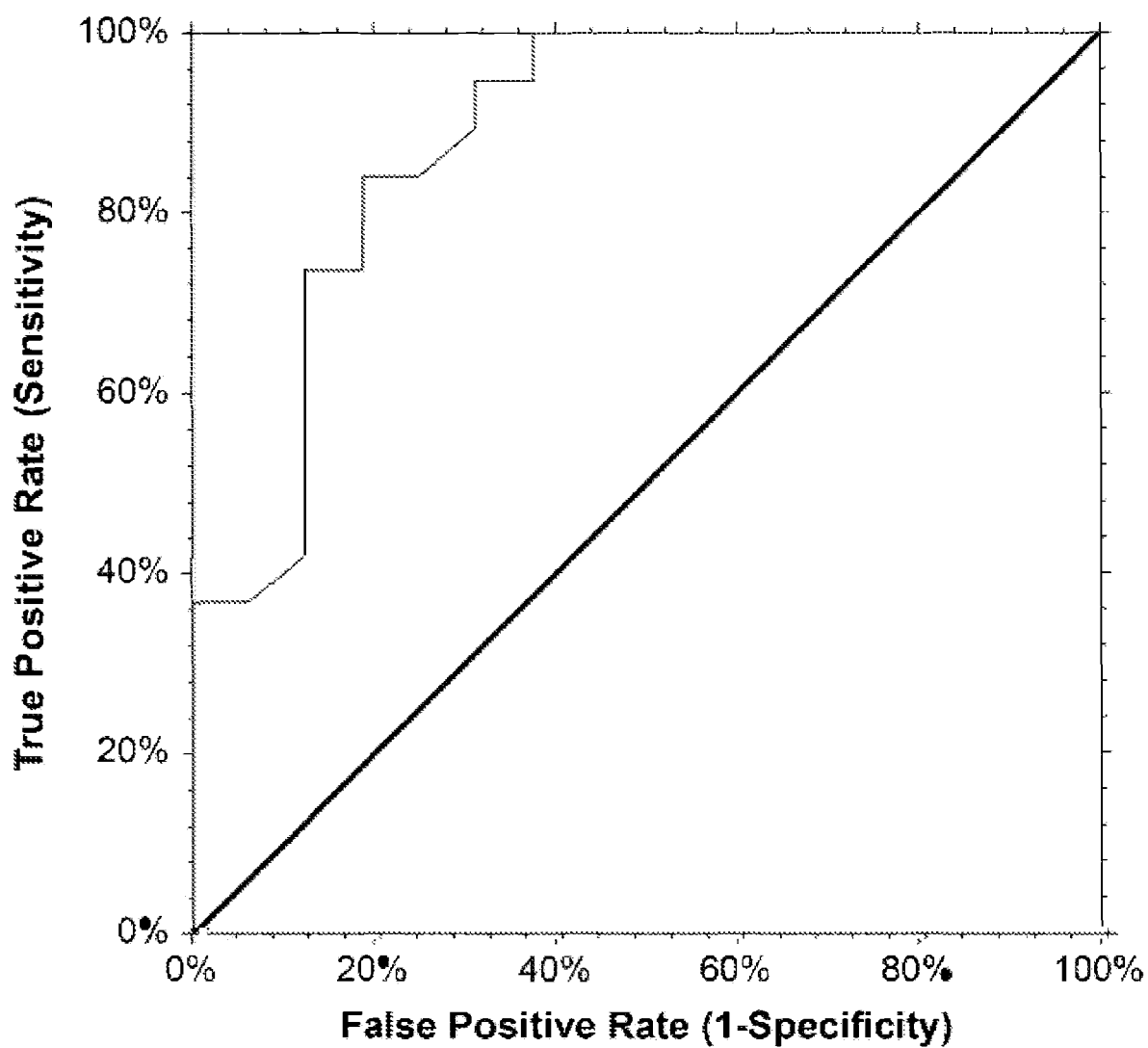
FIG. 4 is a graph representing a receiver operating characteristic (ROC) plot that outlines the fraction of true positives out of the total actual positives (TPR=true positive rate) versus the fraction of false positives out of the total actual negatives (FPR=false positive rate). This plot illustrates the 3-miRNA serum ACR diagnosis signature found in the replication dataset.

The performance of the previously identified 3-miRNA (hsa-miR-125b, hsa-miR-100 and hsa-miR-483) serum multiple marker signature that differentiates ACR from non-ACR was also evaluated in this follow-up study. When using the same coefficients obtained from phase I of the study (presented previously in Example 1) in the logistic regression model to derive a composite score composed of the 3-miRNA serum ACR diagnosis signature, the model also provided excellent ability to differentiate ACR from non-ACR with AUC of 0.885 (95% CI: 0.94-0.83), with 84% sensitivity and 75% specificity (P=0.01) (FIG. 4). 80% of the samples were correctly classified using the 3-miRNA serum ACR diagnosis signature.

TABLE 3

Table 3 lists 20 replicated miRNAs associated with ACR diagnosis detected in the follow up study including 19 ACR and 16 non-ACR samples.

| ID | Fold-Change | Nominal PValue | FDR-BH Pvalue |
|---|---|---|---|
| hsa-miR-483-3p | 6.4822 | 0.0002 | 0.0034 |
| hsa-miR-122-5p | 6.9065 | 0.001 | 0.0069 |
| hsa-miR-885-5p | 6.1095 | 0.0015 | 0.0069 |
| hsa-miR-215 | 4.9237 | 0.0019 | 0.0069 |
| hsa-miR-100-5p | 5.4082 | 0.002 | 0.0069 |
| hsa-miR-34a-5p | 3.7757 | 0.0026 | 0.0069 |
| hsa-miR-152 | 3.9237 | 0.0027 | 0.0069 |
| hsa-miR-192-5p | 3.645 | 0.0029 | 0.0069 |
| hsa-miR-483-5p | 3.7951 | 0.0032 | 0.0069 |
| hsa-miR-148a-3p | 3.4924 | 0.0038 | 0.0069 |
| hsa-miR-194-5p | 3.5736 | 0.0038 | 0.0069 |
| hsa-miR-365a-3p | 3.3761 | 0.0063 | 0.0101 |
| hsa-miR-193a-5p | 2.5899 | 0.007 | 0.0101 |
| hsa-miR-125b-5p | 3.358 | 0.0071 | 0.0101 |
| hsa-miR-30a-5p | 2.8838 | 0.0108 | 0.014 |
| hsa-miR-505-3p | 2.2178 | 0.0112 | 0.014 |
| hsa-miR-378a-3p | 2.0742 | 0.0244 | 0.0288 |
| hsa-miR-99a-5p | 2.8353 | 0.0322 | 0.0357 |
| hsa-miR-874 | 2.3653 | 0.0504 | 0.0531 |
| hsa-miR-497-5p | 2.0478 | 0.1131 | 0.1131 |

Example 4: Additional miRNAs Candidates for Detection and Prediction of Acute Cellular Rejection (ACR)

To identify additional novel miRNAs that are not included in Exiqon Human miRNA Ready-to-Use PCR Panels I and II (v.3) (number of miRNAs included: 752), Qiagen Human miRNome miRNA PCR Array, which contains a much broader panel of 2408 human miRNAs, were employed to screen for additional ACR-associated miRNAs. Fifteen serum samples from the CTOT03 study, including four collected at biopsy proven rejection episodes and eleven collected at non-rejection episodes, were used in this screening. As shown in Table 4, a majority of the top ACR-associated miRNAs identified by the Exiqon platform showed the same direction of association using Qiagen miRNome miRNA PCR array.

TABLE 4

Table 4 lists the top ACR-associated miRNA identified using Exiqon human miRNA panel that were confirmed with Qiagen Human miRNome miRNA PCR Array

| | Exiqon (ITN + CTOT03 130 samples) | | Qiagen (CTOT03 15 samples) | |
|---|---|---|---|---|
| ID | Fold Change | Nominal P-Value | Fold Change | Nominal P-Value |
| hsa-miR-885-5p | 8.8013 | 6.0689E−15 | 6.44 | 0.0318 |
| hsa-miR-122-5p | 6.2466 | 3.0231E−12 | 5.67 | 0.1533 |
| hsa-miR-194-5p | 3.8097 | 9.9819E−12 | 2.18 | 0.2486 |
| hsa-miR-483-3p | 5.4763 | 1.027E−11 | 3.63 | 0.1122 |
| hsa-miR-483-5p | 4.0709 | 2.6528E−11 | 4.89 | 0.0037 |
| hsa-miR-192-5p | 3.9011 | 2.7644E−11 | 2.1 | 0.1623 |
| hsa-miR-30a-5p | 3.1198 | 1.2351E−10 | 3.88 | 0.2258 |
| hsa-miR-193a-5p | 3.1971 | 1.7252E−09 | 1.63 | 0.5229 |
| hsa-miR-378a-3p | 2.4777 | 1.4478E−08 | 1.55 | 0.5225 |
| hsa-miR-21-5p | 2.3019 | 7.9969E−08 | 2.77 | 0.2463 |
| hsa-miR-574-3p | 2.574 | 4.011E−07 | 5.81 | 0.0776 |
| hsa-miR-148a-3p | 2.6657 | 6.1793E−07 | 3.1 | 0.2199 |
| hsa-let-7b-3p | 2.6712 | 2.9049E−06 | 4.89 | 0.0123 |
| hsa-miR-365a-3p | 2.5382 | 0.000010321 | 1.41 | 0.5012 |
| hsa-miR-320c | 2.292 | 0.000014479 | 1.75 | 0.5081 |
| hsa-miR-320b | 2.1672 | 0.000022355 | 1.37 | 0.7152 |
| hsa-miR-378a-5p | 2.2401 | 0.000072482 | 1.44 | 0.6297 |
| hsa-miR-1260a | 2.0542 | 0.000073078 | 3.67 | 0.1225 |

Figure 5:
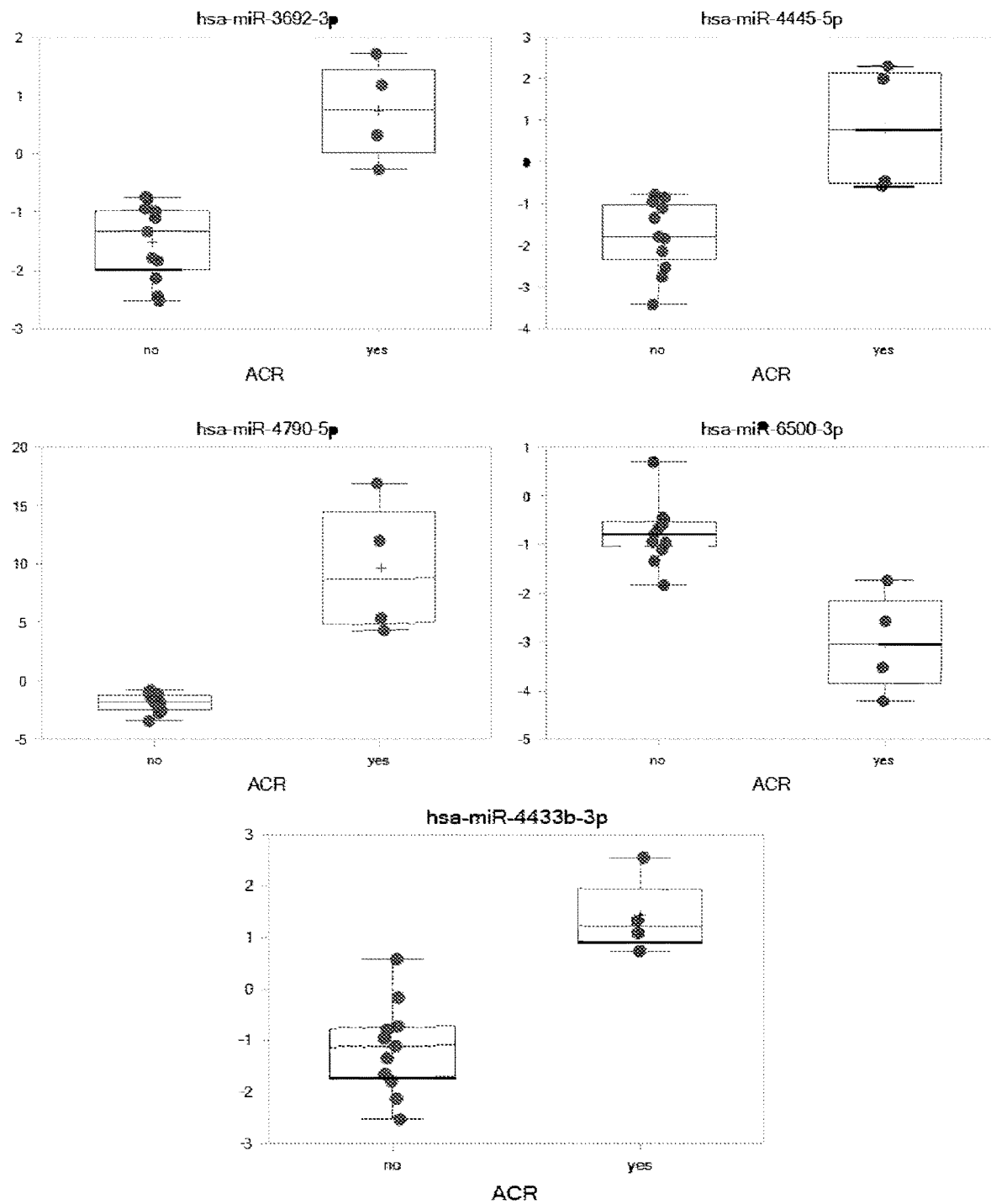
FIG. 5 is a series of box plots depicting the serum expression levels of the top five ACR-associated miRNAs identified by Qiagen Arrays. The Y-axis indicates miRNA expression levels (-dCt) and the X-axis indicates ACR status.

Particularly, by using Qiagen Human miRNome miRNA PCR Array, additional ACR-associated miRNAs, that are not included in the Exiqon panels, were identified (Table 5). Some of the newly-identified miRNAs showed greater fold changes between ACR and non-ACR samples than those originally identified using Exiqon panels and would potentially provide greater discrimination ability if replicated. Examples of box-and-whisker plots for the top five newly-identified miRNAs are shown in FIG. 5.

TABLE 5

Table 5 lists the top ACR-associated miRNA (nominal p < 0.15) identified using Qiagen Human miRNome miRNA PCR Array.

15 CTOT03 samples, 4 ACR, 11 non-ACR

| ID | Fold Change | Nominal P-Value | FDR-BH adjusted P-Value |
|---|---|---|---|
| hsa-miR-4790-5p | 1840.47 | 7.21E−05 | 0.0755 |
| hsa-miR-3692-3p | 4.27 | 0.0006 | 0.2323 |
| hsa-miR-4433b-3p | 5.06 | 0.0009 | 0.2323 |
| hsa-miR-6500-3p | −4.51 | 0.0009 | 0.2323 |
| hsa-miR-4445-5p | 6.78 | 0.0015 | 0.2937 |
| hsa-miR-5194 | 6.61 | 0.002 | 0.2937 |
| hsa-miR-4505 | 12.24 | 0.0024 | 0.2937 |
| hsa-miR-4430 | 4.26 | 0.0027 | 0.2937 |
| hsa-miR-374c-3p | 18708.97 | 0.0028 | 0.2937 |
| hsa-miR-4506 | 4.4 | 0.0033 | 0.2937 |
| hsa-miR-4286 | 9.75 | 0.0037 | 0.2937 |
| hsa-miR-483-5p* | 4.89 | 0.0037 | 0.2937 |
| hsa-miR-6816-5p | 39.27 | 0.0039 | 0.2937 |
| hsa-miR-758-3p* | −17.22 | 0.0039 | 0.2937 |
| hsa-miR-4535 | 5.08 | 0.0047 | 0.3168 |
| hsa-miR-490-3p* | −4.22 | 0.0048 | 0.3168 |
| hsa-miR-6765-5p | 3.12 | 0.0061 | 0.3312 |
| hsa-miR-3197 | 6.5 | 0.0065 | 0.3312 |
| hsa-miR-1271-3p | 4.28 | 0.0067 | 0.3312 |
| hsa-miR-92a-1-5p* | −4.11 | 0.0068 | 0.3312 |
| hsa-miR-8054 | −8.79 | 0.007 | 0.3312 |
| hsa-miR-455-5p* | −15.06 | 0.0077 | 0.3312 |
| hsa-miR-7151-3p | 3.67 | 0.0084 | 0.3312 |
| hsa-miR-628-3p* | −5.16 | 0.0086 | 0.3312 |
| hsa-miR-556-5p* | −8.01 | 0.0088 | 0.3312 |
| hsa-miR-6726-5p | 4.18 | 0.0088 | 0.3312 |
| hsa-miR-1179* | −8.58 | 0.0089 | 0.3312 |
| hsa-miR-3196 | 3.26 | 0.0094 | 0.3312 |
| hsa-miR-6858-5p | 5.43 | 0.0099 | 0.3312 |
| hsa-miR-3673 | −13.01 | 0.01 | 0.3312 |
| hsa-miR-6778-5p | 4.81 | 0.0101 | 0.3312 |
| hsa-miR-4459 | 3.73 | 0.0102 | 0.3312 |
| hsa-miR-380-5p* | −25.15 | 0.0104 | 0.3312 |
| hsa-miR-1273e | 2.95 | 0.0109 | 0.3354 |
| hsa-let-7b-3p* | 4.89 | 0.0123 | 0.3683 |
| hsa-miR-4481 | 3.84 | 0.0132 | 0.3826 |
| hsa-miR-1908-5p | −5.3 | 0.014 | 0.3849 |
| hsa-miR-149-3p* | 4.45 | 0.0142 | 0.3849 |
| hsa-miR-651-3p | −4.85 | 0.0147 | 0.3849 |
| hsa-miR-124-5p* | −6.76 | 0.0148 | 0.3849 |

*miRNA also included in Exiqon Human miRNA Ready-to-Use PCR Panels I and II (v.3)

Example 5: Detailed List of the miRNAs Biomarkers and their Related Target Sequence Selected for ACR Prediction and/or IST Minimization Tolerance

TABLE 6

| Symbol | Accession | MicroRNA Sequence (5'-3') | microRNA Target Sequence (5'-3') |
|---|---|---|---|
| hsa-miR-125b-5p | MIMAT0000423 | ucccugagacccuaacuuguga | tccctgagaccctaacttgtga |
| hsa-miR-100-5p | MIMAT0000098 | aacccguagauccgaacuugug | aacccgtagatccgaacttgtg |
| hsa-miR-483-5p | MIMAT0004761 | aagacgggaggaaagaagggag | aagacgggaggaaagaagggag |
| hsa-miR-885-5p | MIMAT0004947 | uccauuacacuacccugccucu | tccattacactaccctgcctct |
| hsa-miR-122-5p | MIMAT0000421 | uggagugugacaaugguguuug | tggagtgtgacaatggtgtttg |
| hsa-miR-99a-5p | MIMAT0000097 | aacccguagauccgaucuugug | aacccgtagatccgatcttgtg |
| hsa-miR-30a-5p | MIMAT0000087 | uguaaacauccucgacuggaag | tgtaaacatcctcgactggaag |
| hsa-miR-497-5p | MIMAT0002820 | cagcagcacacugugguuugu | cagcagcacactgtggtttgt |
| hsa-miR-194-5p | MIMAT0000460 | uguaacagcaacuccaugugga | tgtaacagcaactccatgtgga |

TABLE 6-continued

| Symbol | Accession | MicroRNA Sequence (5'-3') | microRNA Target Sequence (5'-3') |
|---|---|---|---|
| hsa-miR-34a-5p | MIMAT0000255 | uggcagugucuuagcugguugu | tggcagtgtcttagctggttgt |
| hsa-miR-192-5p | MIMAT0000222 | cugaccuaugaauugacagcc | ctgacctatgaattgacagcc |
| hsa-miR-215 | MI0000291 | aucauucagaaaugguauacaggaaaaugaccuaugaauugacagacaauauagcugaguuugucugucauucuuuaggccaauauucuguaugacugugcuacuucaa | atgacctatgaattgacagac |
| hsa-miR-375 | MIMAT0000728 | uuuguucguucggcucgcguga | tttgttcgttcggctcgcgtga |
| hsa-miR-193a-5p | MIMAT0004614 | ugggucuuugcgggcgagauga | tgggtctttgcgggcgagatga |
| hsa-miR-483-3p | MIMAT0002173 | ucacuccucuccucccgucuu | tcactcctctcctcccgtctt |
| hsa-miR-505-3p | MIMAT0002876 | cgucaacacuugcugguuuccu | cgtcaacacttgctggtttcct |
| hsa-miR-378a-3p | MIMAT0000732 | acuggacuuggagucagaaggc | actggacttggagtcagaagg |
| hsa-miR-193b-3p | MIMAT0002819 | aacuggcccucaaagucccgcu | aactggccctcaaagtcccgct |
| hsa-miR-874 | MI0005532 | uuagcccugcggccccacgcaccagggu aagagagacucucgcuuccugcccuggcccgagggaccgacuggcugggc | ctgccctggcccgagggaccga |
| hsa-miR-365a-3p | MIMAT0000710 | uaaugccccuaaaaauccuuau | taatgcccctaaaaatccttat |
| hsa-miR-152 | MI0000462 | ugucccccccggcccagguucugugauacacuccgacucgggcucuggagcagucagugcaugacagaacuugggccccggaaggacc | tcagtgcatgacagaacttgg |
| hsa-miR-148a-3p | MIMAT0000243 | ucagugcacuacagaacuuugu | tcagtgcactacagaactttgt |
| hsa-miR-29a-5p | MIMAT0004503 | acugauuucuuuuggguguucag | actgatttcttttggtgttcag |
| hsa-miR-146b-5p | MIMAT0002809 | ugagaacugaauuccauaggcu | tgagaactgaattccataggct |
| hsa-miR-424-3p | MIMAT0004749 | caaaacgugaggcgcugcuau | caaaacgtgaggcgctgctat |
| hsa-miR-125a-5p | MIMAT0000443 | ucccugagacccuuuaaccuguga | tccctgagacccttaacctgtga |
| hsa-miR-342-3p | MIMAT0000753 | ucucacacagaaaucgcacccgu | tctcacacagaaatcgcacccgt |
| hsa-miR-150-5p | MIMAT0000451 | ucucccaacccuuguaccagug | tctcccaacccttgtaccagtg |
| hsa-miR-421 | MIMAT0003339 | aucaacagacauuaauugggcgc | atcaacagacattaattgggcgc |
| hsa-miR-223-5p | MIMAT0004570 | cguguauuugacaagcugaguu | cgtgtatttgacaagctgagtt |
| hsa-miR-495-3p | MIMAT0002817 | aaacaaacauggugcacuucuu | aaacaaacatggtgcacttctt |
| hsa-miR-29a-3p | MIMAT0000086 | uagcaccaucugaaaucgguua | tagcaccatctgaaatcggtta |
| hsa-miR-374b-5p | MIMAT0004955 | auauaauacaaccugcuaagug | atataatacaacctgctaagtg |
| hsa-let-7g-5p | MIMAT0000414 | ugagguaguaguuuguacaguu | tgaggtagtagtttgtacagtt |
| hsa-miR-18b-5p | MIMAT0001412 | uaaggugcaucuagugcaguuag | taaggtgcatctagtgcagttag |
| hsa-miR-7-1-3p | MIMAT0004553 | caacaaaucacagucugccaua | caacaaatcacagtctgccata |
| hsa-miR-181c-5p | MIMAT0000258 | aacauucaaccugucggugagu | aacattcaacctgtcggtgagt |
| hsa-miR-454-3p | MIMAT0003885 | uagugcaauauugcuuauagggu | tagtgcaatattgcttataggggt |
| hsa-miR-485-3p | MIMAT0002176 | gucauacacggcucuccucucu | gtcatacacggctctcctctct |
| hsa-miR-374a-5p | MIMAT0004688 | uuauaauacaaccugauaagug | ttataatacaacctgataagtg |
| hsa-miR-99b-5p | MIMAT0000689 | cacccguagaaccgaccuugcg | cacccgtagaaccgaccttgcg |
| hsa-miR-191-5p | MIMAT0000440 | caacggaauccaaaagcagcug | caacggaatcccaaaagcagctg |
| hsa-miR-21-5p | MIMAT0000076 | uagcuuaucagacugauguuga | tagcttatcagactgatgttga |
| hsa-miR-24-3p | MIMAT0000080 | uggcucaguucagcaggaacag | tggctcagttcagcaggaacag |
| hsa-miR-27b-3p | MIMAT0000419 | uucacaguggcuaaguucugc | ttcacagtggctaagttctgc |

TABLE 6-continued

| Symbol | Accession | MicroRNA Sequence (5'-3') | microRNA Target Sequence (5'-3') |
|---|---|---|---|
| hsa-miR-222-3p | MIMAT0000279 | agcuacaucuggcuacugggu | agctacatctggctactggt |
| hsa-miR-20a-3p | MIMAT0004493 | acugcauuaugagcacuuaaag | actgcattatgagcacttaaag |
| hsa-miR-106b-5p | MIMAT0000680 | uaaagugcugacagugcagau | taaagtgctgacagtgcagat |
| hsa-miR-4790-5p | MIMAT0019961 | aucgcuuuaccauucauguu | atcgctttaccattcatgtt |
| hsa-miR-3692-3p | MIMAT0018122 | guuccacacugacacugcagaagu | gttccacactgacactgcagaagt |
| hsa-miR-4433b-3p | MIMAT0030414 | caggaguggggguggggacgu | caggagtgggggtgggacgt |
| hsa-miR-6500-3p | MIMAT0025455 | acacuuguugggaugaccugc | acacttgttgggatgacctgc |
| hsa-miR-4445-5p | MIMAT0018963 | agauuguuucuuuugccgugca | agattgtttcttttgccgtgca |
| hsa-miR-5194 | MIMAT0021125 | ugaggggguuuggaaugggaugg | tgaggggtttggaatgggatgg |
| hsa-miR-4505 | MIMAT0019041 | aggcugggcugggacgga | aggctgggctgggacgga |
| hsa-miR-4430 | MIMAT0018945 | aggcuggagugagcggag | aggctggagtgagcggag |
| hsa-miR-374c-3p | MIMAT0022735 | cacuuagcagguuguauuauau | cacttagcaggttgtattatat |
| hsa-miR-4506 | MIMAT0019042 | aaaugggguggucugaggcaa | aaatgggtggtctgaggcaa |
| hsa-miR-4286 | MIMAT0016916 | accccacuccugguacc | accccactcctggtacc |
| hsa-miR-6816-5p | MIMAT0027532 | uggggcggggcagguccugc | tggggcggggcaggtcctgc |
| hsa-miR-758-3p* | MIMAT0003879 | uuugugaccugguccacuaacc | tttgtgacctggtccactaacc |
| hsa-miR-4535 | MIMAT0019075 | guggaccuggcugggac | gtggacctggctgggac |
| hsa-miR-490-3p* | MIMAT0002806 | caaccuggaggacuccaugcug | caacctggaggactccatgctg |
| hsa-miR-6765-5p | MIMAT0027430 | gugaggcggggccaggaggggugugu | gtgaggcggggccaggagggtgtgt |
| hsa-miR-3197 | MIMAT0015082 | ggaggcgcaggcucggaaaggcg | ggaggcgcaggctcggaaaggcg |
| hsa-miR-1271-3p | MIMAT0022712 | agugccugcuaugugccaggca | agtgcctgctatgtgccaggca |
| hsa-miR-92a-1-5p* | MIMAT0004507 | agguugggaucgguugcaaugcu | aggttgggatcggttgcaatgct |
| hsa-miR-8054 | MIMAT0030981 | gaaaguacagaucggaugggu | gaaagtacagatcggatgggt |
| hsa-miR-455-5p* | MIMAT0003150 | uaugugccuuuggacuacaucg | tatgtgcctttggactacatcg |
| hsa-miR-7151-3p | MIMAT0028213 | cuacaggcuggaaugggcuca | ctacaggctggaatgggctca |
| hsa-miR-628-3p* | MIMAT0003297 | ucuaguaagaguggcagucga | tctagtaagagtggcagtcga |
| hsa-miR-556-5p* | MIMAT0003220 | gaugagcucauuguaauaugag | gatgagctcattgtaatatgag |
| hsa-miR-6726-5p | MIMAT0027353 | cgggagcugggucugcaggu | cgggagctgggtctgcaggt |
| hsa-miR-1179* | MIMAT0005824 | aagcauucuuucauugguugg | aagcattctttcattggttgg |
| hsa-miR-3196 | MIMAT0015080 | cggggcggcagggccuc | cggggcggcagggcctc |
| hsa-miR-6858-5p | MIMAT0027616 | gugaggagggcuggcagggac | gtgaggagggctggcagggac |
| hsa-miR-6778-5p | MIMAT0027456 | aguggaggacaggaggcaggu | agtggaggacaggaggcaggt |
| hsa-miR-4459 | MIMAT0018981 | ccaggaggcggaggagguggag | ccaggaggcggaggaggtggag |
| hsa-miR-380-5p* | MIMAT0000734 | igguugaccauagaacaugcgc | tggttgaccatagaacatgcgc |
| hsa-miR-1273e | MIMAT0018079 | uugcuugaacccaggaagugga | ttgcttgaacccaggaagtgga |
| hsa-let-7b-3p* | MIMAT0004482 | cuauacaaccuacugccuuccc | ctatacaacctactgccttccc |
| hsa-miR-4481 | MIMAT0019015 | ggaguggcuggugguu | ggagtggctggtggtt |
| hsa-miR-1908-5p | MIMAT0007881 | cggcggggacggcgauugguc | cggcggggacggcgattggtc |
| hsa-miR-149-3p* | MIMAT0004609 | agggagggacggggggcugugc | agggagggacgggggctgtgc |

TABLE 6-continued

| Symbol | Accession | MicroRNA Sequence (5'-3') | microRNA Target Sequence (5'-3') |
|---|---|---|---|
| hsa-miR-651-3p | MIMAT0026624 | aaaggaaaguguauccuaaaag | aaaggaaagtgtatcctaaaag |
| hsa-miR-124-5p* | MIMAT0004591 | cguguucacagcggaccuugau | cgtgttcacagcggaccttgat |

The microRNAs' nucleotides sequences in "bold" correspond to the ones that do not have a matching target sequence (i.e. probe) listed in the table 6.
*miRNA also included in Exiqon Human miRNA Ready-to-Use PCR Panels I and II (v.3)

TABLE 7

Table 7 lists the sequence identifiers for the miRNAs biomarkers and their related target sequence (listed in Table 6) selected for ACR prediction and/or IST minimization tolerance.

| Symbol | SEQ. ID for miRNA sequence | SEQ. ID for miRNA Target sequence |
|---|---|---|
| hsa-miR-125b-5p | SEQ ID NO: 1 | SEQ ID NO: 49 |
| hsa-miR-100-5p | SEQ ID NO: 2 | SEQ ID NO: 50 |
| hsa-miR-483-5p | SEQ ID NO: 3 | SEQ ID NO: 51 |
| hsa-miR-885-5p | SEQ ID NO: 4 | SEQ ID NO: 52 |
| hsa-miR-122-5p | SEQ ID NO: 5 | SEQ ID NO: 53 |
| hsa-miR-99a-5p | SEQ ID NO: 6 | SEQ ID NO: 54 |
| hsa-miR-30a-5p | SEQ ID NO: 7 | SEQ ID NO: 55 |
| hsa-miR-497-5p | SEQ ID NO: 8 | SEQ ID NO: 56 |
| hsa-miR-194-5p | SEQ ID NO: 9 | SEQ ID NO: 57 |
| hsa-miR-34a-5p | SEQ ID NO: 10 | SEQ ID NO: 58 |
| hsa-miR-192-5p | SEQ ID NO: 11 | SEQ ID NO: 59 |
| hsa-miR-215 | SEQ ID NO: 12 | SEQ ID NO: 60 |
| hsa-miR-375 | SEQ ID NO: 13 | SEQ ID NO: 61 |
| hsa-miR-193a-5p | SEQ ID NO: 14 | SEQ ID NO: 62 |
| hsa-miR-483-3p | SEQ ID NO: 15 | SEQ ID NO: 63 |
| hsa-miR-505-3p | SEQ ID NO: 16 | SEQ ID NO: 64 |
| hsa-miR-378a-3p | SEQ ID NO: 17 | SEQ ID NO: 65 |
| hsa-miR-193b-3p | SEQ ID NO: 18 | SEQ ID NO: 66 |
| hsa-miR-874 | SEQ ID NO: 19 | SEQ ID NO: 67 |
| hsa-miR-365a-3p | SEQ ID NO: 20 | SEQ ID NO: 68 |
| hsa-miR-152 | SEQ ID NO: 21 | SEQ ID NO: 69 |
| hsa-miR-148a-3p | SEQ ID NO: 22 | SEQ ID NO: 70 |
| hsa-miR-29a-5p | SEQ ID NO: 23 | SEQ ID NO: 71 |
| hsa-miR-146b-5p | SEQ ID NO: 24 | SEQ ID NO: 72 |
| hsa-miR-424-3p | SEQ ID NO: 25 | SEQ ID NO: 73 |
| hsa-miR-125a-5p | SEQ ID NO: 26 | SEQ ID NO: 74 |
| hsa-miR-342-3p | SEQ ID NO: 27 | SEQ ID NO: 75 |
| hsa-miR-150-5p | SEQ ID NO: 28 | SEQ ID NO: 76 |
| hsa-miR-421 | SEQ ID NO: 29 | SEQ ID NO: 77 |
| hsa-miR-223-5p | SEQ ID NO: 30 | SEQ ID NO: 78 |
| hsa-miR-495-3p | SEQ ID NO: 31 | SEQ ID NO: 79 |
| hsa-miR-29a-3p | SEQ ID NO: 32 | SEQ ID NO: 80 |
| hsa-miR-374b-5p | SEQ ID NO: 33 | SEQ ID NO: 81 |
| hsa-let-7g-5p | SEQ ID NO: 34 | SEQ ID NO: 82 |
| hsa-miR-18b-5p | SEQ ID NO: 35 | SEQ ID NO: 83 |
| hsa-miR-7-1-3p | SEQ ID NO: 36 | SEQ ID NO: 84 |
| hsa-miR-181c-5p | SEQ ID NO: 37 | SEQ ID NO: 85 |
| hsa-miR-454-3p | SEQ ID NO: 38 | SEQ ID NO: 86 |
| hsa-miR-485-3p | SEQ ID NO: 39 | SEQ ID NO: 87 |
| hsa-miR-374a-5p | SEQ ID NO: 40 | SEQ ID NO: 88 |
| hsa-miR-99b-5p | SEQ ID NO: 41 | SEQ ID NO: 89 |
| hsa-miR-191-5p | SEQ ID NO: 42 | SEQ ID NO: 90 |
| hsa-miR-21-5p | SEQ ID NO: 43 | SEQ ID NO: 91 |
| hsa-miR-24-3p | SEQ ID NO: 44 | SEQ ID NO: 92 |
| hsa-miR-27b-3p | SEQ ID NO: 45 | SEQ ID NO: 93 |
| hsa-miR-222-3p | SEQ ID NO: 46 | SEQ ID NO: 94 |
| hsa-miR-20a-3p | SEQ ID NO: 47 | SEQ ID NO: 95 |
| hsa-miR-106b-5p | SEQ ID NO: 48 | SEQ ID NO: 96 |
| hsa-miR-4790-5p | SEQ ID NO: 97 | SEQ ID NO: 135 |
| hsa-miR-3692-3p | SEQ ID NO: 98 | SEQ ID NO: 136 |
| hsa-miR-4433b-3p | SEQ ID NO: 99 | SEQ ID NO: 137 |
| hsa-miR-6500-3p | SEQ ID NO: 100 | SEQ ID NO: 138 |
| hsa-miR-4445-5p | SEQ ID NO: 101 | SEQ ID NO: 139 |
| hsa-miR-5194 | SEQ ID NO: 102 | SEQ ID NO: 140 |
| hsa-miR-4505 | SEQ ID NO: 103 | SEQ ID NO: 141 |
| hsa-miR-4430 | SEQ ID NO: 104 | SEQ ID NO: 142 |
| hsa-miR-374c-3p | SEQ ID NO: 105 | SEQ ID NO: 143 |
| hsa-miR-4506 | SEQ ID NO: 106 | SEQ ID NO: 144 |
| hsa-miR-4286 | SEQ ID NO: 107 | SEQ ID NO: 145 |
| hsa-miR-6816-5p | SEQ ID NO: 108 | SEQ ID NO: 146 |
| hsa-miR-758-3p* | SEQ ID NO: 109 | SEQ ID NO: 147 |
| hsa-miR-4535 | SEQ ID NO: 110 | SEQ ID NO: 148 |
| hsa-miR-490-3p* | SEQ ID NO: 111 | SEQ ID NO: 149 |
| hsa-miR-6765-5p | SEQ ID NO: 112 | SEQ ID NO: 150 |
| hsa-miR-3197 | SEQ ID NO: 113 | SEQ ID NO: 151 |
| hsa-miR-1271-3p | SEQ ID NO: 114 | SEQ ID NO: 152 |
| hsa-miR-92a-1-5p* | SEQ ID NO: 115 | SEQ ID NO: 153 |
| hsa-miR-8054 | SEQ ID NO: 116 | SEQ ID NO: 154 |
| hsa-miR-455-5p* | SEQ ID NO: 117 | SEQ ID NO: 155 |
| hsa-miR-7151-3p | SEQ ID NO: 118 | SEQ ID NO: 156 |
| hsa-miR-628-3p* | SEQ ID NO: 119 | SEQ ID NO: 157 |
| hsa-miR-556-5p* | SEQ ID NO: 120 | SEQ ID NO: 158 |
| hsa-miR-6726-5p | SEQ ID NO: 121 | SEQ ID NO: 159 |
| hsa-miR-1179* | SEQ ID NO: 122 | SEQ ID NO: 160 |
| hsa-miR-3196 | SEQ ID NO: 123 | SEQ ID NO: 161 |
| hsa-miR-6858-5p | SEQ ID NO: 124 | SEQ ID NO: 162 |
| hsa-miR-6778-5p | SEQ ID NO: 125 | SEQ ID NO: 163 |
| hsa-miR-4459 | SEQ ID NO: 126 | SEQ ID NO: 164 |
| hsa-miR-380-5p* | SEQ ID NO: 127 | SEQ ID NO: 165 |
| hsa-miR-1273e | SEQ ID NO: 128 | SEQ ID NO: 166 |
| hsa-let-7b-3p* | SEQ ID NO: 129 | SEQ ID NO: 167 |
| hsa-miR-4481 | SEQ ID NO: 130 | SEQ ID NO: 168 |
| hsa-miR-1908-5p | SEQ ID NO: 131 | SEQ ID NO: 169 |
| hsa-miR-149-3p* | SEQ ID NO: 132 | SEQ ID NO: 170 |
| hsa-miR-651-3p | SEQ ID NO: 133 | SEQ ID NO: 171 |
| hsa-miR-124-5p* | SEQ ID NO: 134 | SEQ ID NO: 172 |

The disclosures of each and every patent, patent application, and publication cited herein are hereby incorporated herein by reference in their entirety.

While the present invention has been disclosed with reference to specific embodiments, it is apparent that other embodiments and variations of the present invention may be devised by others skilled in the art without departing from the true spirit and scope of the invention. The appended claims are intended to be construed to include all such embodiments and equivalent variations.

What is claimed is:

1. A method for detecting or predicting transplant rejection of a transplanted liver in a subject being administered a dose of an immunosuppressant, the method comprising:
   i) determining a level of expression of hsa-miR-483-5p (SEQ ID NO: 3), hsa-miR-885-5p (SEQ ID NO: 4) and hsa-miR-122-5p (SEQ ID NO: 5) in a sample from the subject wherein the sample is selected from the group consisting of blood, plasma and serum;
   ii) comparing the level of expression of hsa-miR-483-5p (SEQ ID NO: 3), hsa-miR-885-5p (SEQ ID NO: 4) and hsa-miR-122-5p (SEQ ID NO: 5) in the sample from the subject relative to a baseline level in a control wherein an increase in the level of expression in the sample from the level of the at least one miRNA in the control is indicative of an acute transplant rejection;
   iii) wherein when acute transplant rejection is indicated, the rejection is treated by increasing the dose of the immunosuppressant; and
   iv) wherein when acute transplant rejection is not indicated in step ii., decreasing or minimizing the dose of the immunosuppressant.

2. The method of claim 1, wherein the acute transplant rejection comprises acute cellular rejection (ACR).

3. The method of claim 1, wherein the subject is a mammal.

4. The method of claim 3, wherein the mammal is a human.

5. The method of claim 1, wherein the level of expression in the sample is higher than the level in the control by at least 1 fold.

6. The method of claim 1, wherein the comparison of the level of miRNA expression in a sample relative to the baseline level is computed in a regression model to indicate a trajectory of acute rejection of the transplanted organ.

7. The method of claim 1, further comprising the step of repeating steps i. to iii.

* * * * *

SEQUENCE LISTING

<160> NUMBER OF SEQ ID NOS: 172

<210> SEQ ID NO 1
<211> LENGTH: 22
<212> TYPE: RNA
<213> ORGANISM: Homo Sapiens

<400> SEQUENCE: 1
ucccugagac ccuaacuugu ga                                                22

<210> SEQ ID NO 2
<211> LENGTH: 22
<212> TYPE: RNA
<213> ORGANISM: Homo Sapiens

<400> SEQUENCE: 2
aacccguaga uccgaacuug ug                                                22

<210> SEQ ID NO 3
<211> LENGTH: 22
<212> TYPE: RNA
<213> ORGANISM: Homo Sapiens

<400> SEQUENCE: 3
aagacgggag gaaagaaggg ag                                                22

<210> SEQ ID NO 4
<211> LENGTH: 22
<212> TYPE: RNA
<213> ORGANISM: Homo Sapiens

<400> SEQUENCE: 4
uccauuacac uacccugccu cu                                                22

<210> SEQ ID NO 5
<211> LENGTH: 22
<212> TYPE: RNA
<213> ORGANISM: Homo Sapiens

<400> SEQUENCE: 5
uggaguguga caauggyguu ug                                                22

<210> SEQ ID NO 6
<211> LENGTH: 22
<212> TYPE: RNA
<213> ORGANISM: Homo Sapiens

<400> SEQUENCE: 6
aacccguaga uccgaucuug ug                                                22

<210> SEQ ID NO 7
<211> LENGTH: 22
<212> TYPE: RNA
<213> ORGANISM: Homo Sapiens

<400> SEQUENCE: 7
uguaaacauc cucgacugga ag                                                22

<210> SEQ ID NO 8
<211> LENGTH: 21
<212> TYPE: RNA
<213> ORGANISM: Homo Sapiens

<400> SEQUENCE: 8
cagcagcaca cugugguuug u                                              21

<210> SEQ ID NO 9
<211> LENGTH: 22
<212> TYPE: RNA
<213> ORGANISM: Homo Sapiens

<400> SEQUENCE: 9
uguaacagca acuccaugug ga                                             22

<210> SEQ ID NO 10
<211> LENGTH: 22
<212> TYPE: RNA
<213> ORGANISM: Homo Sapiens

<400> SEQUENCE: 10
uggcaguguc uuagcugguu gu                                             22

<210> SEQ ID NO 11
<211> LENGTH: 21
<212> TYPE: RNA
<213> ORGANISM: Homo Sapiens

<400> SEQUENCE: 11
cugaccuaug aauugacagc c                                              21

<210> SEQ ID NO 12
<211> LENGTH: 110
<212> TYPE: RNA
<213> ORGANISM: Homo Sapiens

<400> SEQUENCE: 12
aucauucaga aaugguauac aggaaaauga ccuaugaauu gacagacaau auagcugagu    60
uugucuguca uucuuuagg ccaauauucu guaugacugu gcuacuucaa               110

<210> SEQ ID NO 13
<211> LENGTH: 22
<212> TYPE: RNA
<213> ORGANISM: Homo Sapiens

<400> SEQUENCE: 13
uuuguucguu cggcucgcgu ga                                             22

<210> SEQ ID NO 14
<211> LENGTH: 22
<212> TYPE: RNA
<213> ORGANISM: Homo Sapiens

<400> SEQUENCE: 14
ugggucuuug cgggcgagau ga                                             22

<210> SEQ ID NO 15
<211> LENGTH: 21
<212> TYPE: RNA
<213> ORGANISM: Homo Sapiens

<400> SEQUENCE: 15
ucacuccucu ccucccgucu u                                              21

<210> SEQ ID NO 16
<211> LENGTH: 22
<212> TYPE: RNA

<213> ORGANISM: Homo Sapiens

<400> SEQUENCE: 16
cgucaacacu ugcugguuuc cu                                        22

<210> SEQ ID NO 17
<211> LENGTH: 22
<212> TYPE: RNA
<213> ORGANISM: Homo Sapiens

<400> SEQUENCE: 17
acuggacuug gagucagaag gc                                        22

<210> SEQ ID NO 18
<211> LENGTH: 22
<212> TYPE: RNA
<213> ORGANISM: Homo Sapiens

<400> SEQUENCE: 18
aacuggcccu caaagucccg cu                                        22

<210> SEQ ID NO 19
<211> LENGTH: 78
<212> TYPE: RNA
<213> ORGANISM: Homo Sapiens

<400> SEQUENCE: 19
uuagcccugc ggccccacgc accaggguaa gagagacucu cgcuuccugc ccuggcccga    60
gggaccgacu ggcugggc                                             78

<210> SEQ ID NO 20
<211> LENGTH: 22
<212> TYPE: RNA
<213> ORGANISM: Homo Sapiens

<400> SEQUENCE: 20
uaaugccccu aaaaauccuu au                                        22

<210> SEQ ID NO 21
<211> LENGTH: 87
<212> TYPE: RNA
<213> ORGANISM: Homo Sapiens

<400> SEQUENCE: 21 ugucccccc ggcccagguu cugugauaca cuccgacucg ggcucuggag cagucagugc    60
augacagaac uugggcccgg aaggacc                                   87

<210> SEQ ID NO 22
<211> LENGTH: 22
<212> TYPE: RNA
<213> ORGANISM: Homo Sapiens

<400> SEQUENCE: 22
ucagugcacu acagaacuuu gu                                        22

<210> SEQ ID NO 23
<211> LENGTH: 22
<212> TYPE: RNA
<213> ORGANISM: Homo Sapiens

<400> SEQUENCE: 23
acugauuucu uuugguguuc ag                                        22

<210> SEQ ID NO 24
<211> LENGTH: 22
<212> TYPE: RNA
<213> ORGANISM: Homo Sapiens

<400> SEQUENCE: 24
ugagaacuga auuccauagg cu                                                22

<210> SEQ ID NO 25
<211> LENGTH: 21
<212> TYPE: RNA
<213> ORGANISM: Homo Sapiens

<400> SEQUENCE: 25
caaaacguga ggcgcugcua u                                                 21

<210> SEQ ID NO 26
<211> LENGTH: 24
<212> TYPE: RNA
<213> ORGANISM: Homo Sapiens

<400> SEQUENCE: 26
ucccugagac ccuuuaaccu guga                                              24

<210> SEQ ID NO 27
<211> LENGTH: 23
<212> TYPE: RNA
<213> ORGANISM: Homo Sapiens

<400> SEQUENCE: 27
ucucacacag aaaucgcacc cgu                                               23

<210> SEQ ID NO 28
<211> LENGTH: 22
<212> TYPE: RNA
<213> ORGANISM: Homo Sapiens

<400> SEQUENCE: 28
ucucccaacc cuuguaccag ug                                                22

<210> SEQ ID NO 29
<211> LENGTH: 23
<212> TYPE: RNA
<213> ORGANISM: Homo Sapiens

<400> SEQUENCE: 29
aucaacagac auuaauuggg cgc                                               23

<210> SEQ ID NO 30
<211> LENGTH: 22
<212> TYPE: RNA
<213> ORGANISM: Homo Sapiens

<400> SEQUENCE: 30
cguguauuug acaagcugag uu                                                22

<210> SEQ ID NO 31
<211> LENGTH: 22
<212> TYPE: RNA
<213> ORGANISM: Homo Sapiens

<400> SEQUENCE: 31

```
aaacaaacau ggugcacuuc uu                                    22

<210> SEQ ID NO 32
<211> LENGTH: 22
<212> TYPE: RNA
<213> ORGANISM: Homo Sapiens

<400> SEQUENCE: 32
uagcaccauc ugaaaucggu ua                                    22

<210> SEQ ID NO 33
<211> LENGTH: 22
<212> TYPE: RNA
<213> ORGANISM: Homo Sapiens

<400> SEQUENCE: 33
auauaauaca accugcuaag ug                                    22

<210> SEQ ID NO 34
<211> LENGTH: 22
<212> TYPE: RNA
<213> ORGANISM: Homo Sapiens

<400> SEQUENCE: 34
ugagguagua guuuguacag uu                                    22

<210> SEQ ID NO 35
<211> LENGTH: 23
<212> TYPE: RNA
<213> ORGANISM: Homo Sapiens

<400> SEQUENCE: 35
uaaggugcau cuagugcagu uag                                   23

<210> SEQ ID NO 36
<211> LENGTH: 22
<212> TYPE: RNA
<213> ORGANISM: Homo Sapiens

<400> SEQUENCE: 36
caacaaauca cagucugcca ua                                    22

<210> SEQ ID NO 37
<211> LENGTH: 22
<212> TYPE: RNA
<213> ORGANISM: Homo Sapiens

<400> SEQUENCE: 37
aacauucaac cugucgguga gu                                    22

<210> SEQ ID NO 38
<211> LENGTH: 23
<212> TYPE: RNA
<213> ORGANISM: Homo Sapiens

<400> SEQUENCE: 38
uagugcaaua uugcuuauag ggu                                   23

<210> SEQ ID NO 39
<211> LENGTH: 22
<212> TYPE: RNA
<213> ORGANISM: Homo Sapiens

<400> SEQUENCE: 39
```

```
gucauacacg gcucuccucu cu                                          22

<210> SEQ ID NO 40
<211> LENGTH: 22
<212> TYPE: RNA
<213> ORGANISM: Homo Sapiens

<400> SEQUENCE: 40
uuauaauaca accugauaag ug                                          22

<210> SEQ ID NO 41
<211> LENGTH: 22
<212> TYPE: RNA
<213> ORGANISM: Homo Sapiens

<400> SEQUENCE: 41
cacccguaga accgaccuug cg                                          22

<210> SEQ ID NO 42
<211> LENGTH: 23
<212> TYPE: RNA
<213> ORGANISM: Homo Sapiens

<400> SEQUENCE: 42
caacggaauc ccaaaagcag cug                                         23

<210> SEQ ID NO 43
<211> LENGTH: 22
<212> TYPE: RNA
<213> ORGANISM: Homo Sapiens

<400> SEQUENCE: 43
uagcuuauca gacugauguu ga                                          22

<210> SEQ ID NO 44
<211> LENGTH: 22
<212> TYPE: RNA
<213> ORGANISM: Homo Sapiens

<400> SEQUENCE: 44
uggcucaguu cagcaggaac ag                                          22

<210> SEQ ID NO 45
<211> LENGTH: 21
<212> TYPE: RNA
<213> ORGANISM: Homo Sapiens

<400> SEQUENCE: 45
uucacagugg cuaaguucug c                                           21

<210> SEQ ID NO 46
<211> LENGTH: 21
<212> TYPE: RNA
<213> ORGANISM: Homo Sapiens

<400> SEQUENCE: 46
agcuacaucu ggcuacuggg u                                           21

<210> SEQ ID NO 47
<211> LENGTH: 22
<212> TYPE: RNA
<213> ORGANISM: Homo Sapiens
```

-continued

```
<400> SEQUENCE: 47
acugcauuau gagcacuuaa ag                                              22

<210> SEQ ID NO 48
<211> LENGTH: 21
<212> TYPE: RNA
<213> ORGANISM: Homo Sapiens

<400> SEQUENCE: 48
uaaagugcug acagugcaga u                                               21

<210> SEQ ID NO 49
<211> LENGTH: 22
<212> TYPE: DNA
<213> ORGANISM: Artificial Sequence
<220> FEATURE:
<223> OTHER INFORMATION: Probe

<400> SEQUENCE: 49
tccctgagac cctaacttgt ga                                              22

<210> SEQ ID NO 50
<211> LENGTH: 22
<212> TYPE: DNA
<213> ORGANISM: Artificial sequence
<220> FEATURE:
<223> OTHER INFORMATION: Probe

<400> SEQUENCE: 50
aacccgtaga tccgaacttg tg                                              22

<210> SEQ ID NO 51
<211> LENGTH: 22
<212> TYPE: DNA
<213> ORGANISM: Artificial sequence
<220> FEATURE:
<223> OTHER INFORMATION: Probe

<400> SEQUENCE: 51
aagacgggag gaaagaaggg ag                                              22

<210> SEQ ID NO 52
<211> LENGTH: 22
<212> TYPE: DNA
<213> ORGANISM: Artificial sequence
<220> FEATURE:
<223> OTHER INFORMATION: Probe

<400> SEQUENCE: 52
tccattacac taccctgcct ct                                              22

<210> SEQ ID NO 53
<211> LENGTH: 22
<212> TYPE: DNA
<213> ORGANISM: Artificial sequence
<220> FEATURE:
<223> OTHER INFORMATION: Probe

<400> SEQUENCE: 53
tggagtgtga caatggtgtt tg                                              22

<210> SEQ ID NO 54
<211> LENGTH: 22
<212> TYPE: DNA
<213> ORGANISM: Artificial sequence
```

```
<220> FEATURE:
<223> OTHER INFORMATION: Probe

<400> SEQUENCE: 54
aacccgtaga tccgatcttg tg                                              22

<210> SEQ ID NO 55
<211> LENGTH: 22
<212> TYPE: DNA
<213> ORGANISM: Artificial sequence
<220> FEATURE:
<223> OTHER INFORMATION: Probe

<400> SEQUENCE: 55
tgtaaacatc ctcgactgga ag                                              22

<210> SEQ ID NO 56
<211> LENGTH: 21
<212> TYPE: DNA
<213> ORGANISM: Artificial sequence
<220> FEATURE:
<223> OTHER INFORMATION: Probe

<400> SEQUENCE: 56
cagcagcaca ctgtggtttg t                                               21

<210> SEQ ID NO 57
<211> LENGTH: 22
<212> TYPE: DNA
<213> ORGANISM: Artificial sequence
<220> FEATURE:
<223> OTHER INFORMATION: Probe

<400> SEQUENCE: 57
tgtaacagca actccatgtg ga                                              22

<210> SEQ ID NO 58
<211> LENGTH: 22
<212> TYPE: DNA
<213> ORGANISM: Artificial sequence
<220> FEATURE:
<223> OTHER INFORMATION: Probe

<400> SEQUENCE: 58
tggcagtgtc ttagctggtt gt                                              22

<210> SEQ ID NO 59
<211> LENGTH: 21
<212> TYPE: DNA
<213> ORGANISM: Artificial sequence
<220> FEATURE:
<223> OTHER INFORMATION: Probe

<400> SEQUENCE: 59
ctgacctatg aattgacagc c                                               21

<210> SEQ ID NO 60
<211> LENGTH: 21
<212> TYPE: DNA
<213> ORGANISM: Artificial sequence
<220> FEATURE:
<223> OTHER INFORMATION: Probe

<400> SEQUENCE: 60
atgacctatg aattgacaga c                                               21
```

```
<210> SEQ ID NO 61
<211> LENGTH: 22
<212> TYPE: DNA
<213> ORGANISM: Artificial sequence
<220> FEATURE:
<223> OTHER INFORMATION: Probe

<400> SEQUENCE: 61
tttgttcgtt cggctcgcgt ga                                              22

<210> SEQ ID NO 62
<211> LENGTH: 22
<212> TYPE: DNA
<213> ORGANISM: Artificial sequence
<220> FEATURE:
<223> OTHER INFORMATION: Probe

<400> SEQUENCE: 62
tgggtctttg cgggcgagat ga                                              22

<210> SEQ ID NO 63
<211> LENGTH: 21
<212> TYPE: DNA
<213> ORGANISM: Artificial sequence
<220> FEATURE:
<223> OTHER INFORMATION: Probe

<400> SEQUENCE: 63
tcactcctct cctcccgtct t                                               21

<210> SEQ ID NO 64
<211> LENGTH: 22
<212> TYPE: DNA
<213> ORGANISM: Artificial sequence
<220> FEATURE:
<223> OTHER INFORMATION: Probe

<400> SEQUENCE: 64
cgtcaacact tgctggtttc ct                                              22

<210> SEQ ID NO 65
<211> LENGTH: 21
<212> TYPE: DNA
<213> ORGANISM: Artificial sequence
<220> FEATURE:
<223> OTHER INFORMATION: Probe

<400> SEQUENCE: 65
actggacttg gagtcagaag g                                               21

<210> SEQ ID NO 66
<211> LENGTH: 22
<212> TYPE: DNA
<213> ORGANISM: Artificial sequence
<220> FEATURE:
<223> OTHER INFORMATION: Probe

<400> SEQUENCE: 66
aactggccct caaagtcccg ct                                              22

<210> SEQ ID NO 67
<211> LENGTH: 22
<212> TYPE: DNA
<213> ORGANISM: Artificial sequence
<220> FEATURE:
<223> OTHER INFORMATION: Probe
```

```
<400> SEQUENCE: 67
ctgccctggc ccgagggacc ga                                               22

<210> SEQ ID NO 68
<211> LENGTH: 22
<212> TYPE: DNA
<213> ORGANISM: Artificial sequence
<220> FEATURE:
<223> OTHER INFORMATION: Probe

<400> SEQUENCE: 68
taatgcccct aaaaatcctt at                                               22

<210> SEQ ID NO 69
<211> LENGTH: 21
<212> TYPE: DNA
<213> ORGANISM: Artificial sequence
<220> FEATURE:
<223> OTHER INFORMATION: Probe

<400> SEQUENCE: 69
tcagtgcatg acagaacttg g                                                21

<210> SEQ ID NO 70
<211> LENGTH: 22
<212> TYPE: DNA
<213> ORGANISM: Artificial sequence
<220> FEATURE:
<223> OTHER INFORMATION: Probe

<400> SEQUENCE: 70
tcagtgcact acagaacttt gt                                               22

<210> SEQ ID NO 71
<211> LENGTH: 22
<212> TYPE: DNA
<213> ORGANISM: Artificial sequence
<220> FEATURE:
<223> OTHER INFORMATION: Probe

<400> SEQUENCE: 71
actgatttct tttggtgttc ag                                               22

<210> SEQ ID NO 72
<211> LENGTH: 22
<212> TYPE: DNA
<213> ORGANISM: Artificial sequence
<220> FEATURE:
<223> OTHER INFORMATION: Probe

<400> SEQUENCE: 72
tgagaactga attccatagg ct                                               22

<210> SEQ ID NO 73
<211> LENGTH: 21
<212> TYPE: DNA
<213> ORGANISM: Artificial sequence
<220> FEATURE:
<223> OTHER INFORMATION: Probe

<400> SEQUENCE: 73
caaaacgtga ggcgctgcta t                                                21

<210> SEQ ID NO 74
```

```
<211> LENGTH: 24
<212> TYPE: DNA
<213> ORGANISM: Artificial sequence
<220> FEATURE:
<223> OTHER INFORMATION: Probe

<400> SEQUENCE: 74
tccctgagac cctttaacct gtga                                              24

<210> SEQ ID NO 75
<211> LENGTH: 23
<212> TYPE: DNA
<213> ORGANISM: Artificial sequence
<220> FEATURE:
<223> OTHER INFORMATION: Probe

<400> SEQUENCE: 75
tctcacacag aaatcgcacc cgt                                               23

<210> SEQ ID NO 76
<211> LENGTH: 22
<212> TYPE: DNA
<213> ORGANISM: Artificial sequence
<220> FEATURE:
<223> OTHER INFORMATION: Probe

<400> SEQUENCE: 76
tctcccaacc cttgtaccag tg                                                22

<210> SEQ ID NO 77
<211> LENGTH: 23
<212> TYPE: DNA
<213> ORGANISM: Artificial sequence
<220> FEATURE:
<223> OTHER INFORMATION: Probe

<400> SEQUENCE: 77
atcaacagac attaattggg cgc                                               23

<210> SEQ ID NO 78
<211> LENGTH: 22
<212> TYPE: DNA
<213> ORGANISM: Artificial sequence
<220> FEATURE:
<223> OTHER INFORMATION: Probe

<400> SEQUENCE: 78
cgtgtatttg acaagctgag tt                                                22

<210> SEQ ID NO 79
<211> LENGTH: 22
<212> TYPE: DNA
<213> ORGANISM: Artificial sequence
<220> FEATURE:
<223> OTHER INFORMATION: Probe

<400> SEQUENCE: 79
aaacaaacat ggtgcacttc tt                                                22

<210> SEQ ID NO 80
<211> LENGTH: 22
<212> TYPE: DNA
<213> ORGANISM: Artificial sequence
<220> FEATURE:
<223> OTHER INFORMATION: Probe

<400> SEQUENCE: 80
```
tagcaccatc tgaaatcggt ta                                        22

<210> SEQ ID NO 81
<211> LENGTH: 22
<212> TYPE: DNA
<213> ORGANISM: Artificial sequence
<220> FEATURE:
<223> OTHER INFORMATION: Probe

<400> SEQUENCE: 81
atataataca acctgctaag tg                                        22

<210> SEQ ID NO 82
<211> LENGTH: 22
<212> TYPE: DNA
<213> ORGANISM: Artificial sequence
<220> FEATURE:
<223> OTHER INFORMATION: Probe

<400> SEQUENCE: 82
tgaggtagta gtttgtacag tt                                        22

<210> SEQ ID NO 83
<211> LENGTH: 23
<212> TYPE: DNA
<213> ORGANISM: Artificial sequence
<220> FEATURE:
<223> OTHER INFORMATION: Probe

<400> SEQUENCE: 83
taaggtgcat ctagtgcagt tag                                       23

<210> SEQ ID NO 84
<211> LENGTH: 22
<212> TYPE: DNA
<213> ORGANISM: Artificial sequence
<220> FEATURE:
<223> OTHER INFORMATION: Probe

<400> SEQUENCE: 84
caacaaatca cagtctgcca ta                                        22

<210> SEQ ID NO 85
<211> LENGTH: 22
<212> TYPE: DNA
<213> ORGANISM: Artificial sequence
<220> FEATURE:
<223> OTHER INFORMATION: Probe

<400> SEQUENCE: 85
aacattcaac ctgtcggtga gt                                        22

<210> SEQ ID NO 86
<211> LENGTH: 23
<212> TYPE: DNA
<213> ORGANISM: Artificial sequence
<220> FEATURE:
<223> OTHER INFORMATION: Probe

<400> SEQUENCE: 86
tagtgcaata ttgcttatag ggt                                       23

<210> SEQ ID NO 87
<211> LENGTH: 22
<212> TYPE: DNA

```
<213> ORGANISM: Artificial sequence
<220> FEATURE:
<223> OTHER INFORMATION: Probe

<400> SEQUENCE: 87
gtcatacacg gctctcctct ct                                              22

<210> SEQ ID NO 88
<211> LENGTH: 22
<212> TYPE: DNA
<213> ORGANISM: Artificial sequence
<220> FEATURE:
<223> OTHER INFORMATION: Probe

<400> SEQUENCE: 88
ttataataca acctgataag tg                                              22

<210> SEQ ID NO 89
<211> LENGTH: 22
<212> TYPE: DNA
<213> ORGANISM: Artificial sequence
<220> FEATURE:
<223> OTHER INFORMATION: Probe

<400> SEQUENCE: 89
cacccgtaga accgaccttg cg                                              22

<210> SEQ ID NO 90
<211> LENGTH: 23
<212> TYPE: DNA
<213> ORGANISM: Artificial sequence
<220> FEATURE:
<223> OTHER INFORMATION: Probe

<400> SEQUENCE: 90
caacggaatc ccaaaagcag ctg                                             23

<210> SEQ ID NO 91
<211> LENGTH: 22
<212> TYPE: DNA
<213> ORGANISM: Artificial sequence
<220> FEATURE:
<223> OTHER INFORMATION: Probe

<400> SEQUENCE: 91
tagcttatca gactgatgtt ga                                              22

<210> SEQ ID NO 92
<211> LENGTH: 22
<212> TYPE: DNA
<213> ORGANISM: Artificial sequence
<220> FEATURE:
<223> OTHER INFORMATION: Probe

<400> SEQUENCE: 92
tggctcagtt cagcaggaac ag                                              22

<210> SEQ ID NO 93
<211> LENGTH: 21
<212> TYPE: DNA
<213> ORGANISM: Artificial sequence
<220> FEATURE:
<223> OTHER INFORMATION: Probe

<400> SEQUENCE: 93
ttcacagtgg ctaagttctg c                                               21
```

```
<210> SEQ ID NO 94
<211> LENGTH: 21
<212> TYPE: DNA
<213> ORGANISM: Artificial sequence
<220> FEATURE:
<223> OTHER INFORMATION: Probe

<400> SEQUENCE: 94
agctacatct ggctactggg t                                              21

<210> SEQ ID NO 95
<211> LENGTH: 22
<212> TYPE: DNA
<213> ORGANISM: Artificial sequence
<220> FEATURE:
<223> OTHER INFORMATION: Probe

<400> SEQUENCE: 95
actgcattat gagcacttaa ag                                             22

<210> SEQ ID NO 96
<211> LENGTH: 21
<212> TYPE: DNA
<213> ORGANISM: Artificial sequence
<220> FEATURE:
<223> OTHER INFORMATION: Probe

<400> SEQUENCE: 96
taaagtgctg acagtgcaga t                                              21

<210> SEQ ID NO 97
<211> LENGTH: 20
<212> TYPE: RNA
<213> ORGANISM: Homo Sapiens

<400> SEQUENCE: 97
aucgcuuuac cauucauguu                                                20

<210> SEQ ID NO 98
<211> LENGTH: 24
<212> TYPE: RNA
<213> ORGANISM: Homo Sapiens

<400> SEQUENCE: 98
guuccacacu gacacugcag aagu                                           24

<210> SEQ ID NO 99
<211> LENGTH: 21
<212> TYPE: RNA
<213> ORGANISM: Homo Sapiens

<400> SEQUENCE: 99
caggaguggg ggugggacg u                                               21

<210> SEQ ID NO 100
<211> LENGTH: 21
<212> TYPE: RNA
<213> ORGANISM: Homo Sapiens

<400> SEQUENCE: 100
acacuuguug ggaugaccug c                                              21

<210> SEQ ID NO 101
```

```
<211> LENGTH: 22
<212> TYPE: RNA
<213> ORGANISM: Homo Sapiens

<400> SEQUENCE: 101
agauuguuuc uuuugccgug ca                                              22

<210> SEQ ID NO 102
<211> LENGTH: 22
<212> TYPE: RNA
<213> ORGANISM: Homo Sapiens

<400> SEQUENCE: 102 ugaggguuu ggaaugggau gg                                               22

<210> SEQ ID NO 103
<211> LENGTH: 18
<212> TYPE: RNA
<213> ORGANISM: Homo Sapiens

<400> SEQUENCE: 103
aggcugggcu gggacgga                                                   18

<210> SEQ ID NO 104
<211> LENGTH: 18
<212> TYPE: RNA
<213> ORGANISM: Homo Sapiens

<400> SEQUENCE: 104
aggcuggagu gagcggag                                                   18

<210> SEQ ID NO 105
<211> LENGTH: 22
<212> TYPE: RNA
<213> ORGANISM: Homo Sapiens

<400> SEQUENCE: 105
cacuuagcag guuguauuau au                                              22

<210> SEQ ID NO 106
<211> LENGTH: 20
<212> TYPE: RNA
<213> ORGANISM: Homo Sapiens

<400> SEQUENCE: 106
aaaugggugg ucugaggcaa                                                 20

<210> SEQ ID NO 107
<211> LENGTH: 17
<212> TYPE: RNA
<213> ORGANISM: Homo Sapiens

<400> SEQUENCE: 107
accccacucc ugguacc                                                    17

<210> SEQ ID NO 108
<211> LENGTH: 21
<212> TYPE: RNA
<213> ORGANISM: Homo Sapiens

<400> SEQUENCE: 108
uggggcgggg cagguccug c                                                21
```

```
<210> SEQ ID NO 109
<211> LENGTH: 22
<212> TYPE: RNA
<213> ORGANISM: Homo Sapiens

<400> SEQUENCE: 109
uuugugaccu gguccacuaa cc                                              22

<210> SEQ ID NO 110
<211> LENGTH: 17
<212> TYPE: RNA
<213> ORGANISM: Homo Sapiens

<400> SEQUENCE: 110
guggaccugg cugggac                                                    17

<210> SEQ ID NO 111
<211> LENGTH: 22
<212> TYPE: RNA
<213> ORGANISM: Homo Sapiens

<400> SEQUENCE: 111
caaccuggag gacuccaugc ug                                              22

<210> SEQ ID NO 112
<211> LENGTH: 25
<212> TYPE: RNA
<213> ORGANISM: Homo Sapiens

<400> SEQUENCE: 112
gugaggcggg gccaggaggg ugugu                                           25

<210> SEQ ID NO 113
<211> LENGTH: 23
<212> TYPE: RNA
<213> ORGANISM: Homo Sapiens

<400> SEQUENCE: 113
ggaggcgcag gcucggaaag gcg                                             23

<210> SEQ ID NO 114
<211> LENGTH: 22
<212> TYPE: RNA
<213> ORGANISM: Homo Sapiens

<400> SEQUENCE: 114
agugccugcu augugccagg ca                                              22

<210> SEQ ID NO 115
<211> LENGTH: 23
<212> TYPE: RNA
<213> ORGANISM: Homo Sapiens

<400> SEQUENCE: 115
agguugggau cgguugcaau gcu                                             23

<210> SEQ ID NO 116
<211> LENGTH: 21
<212> TYPE: RNA
<213> ORGANISM: Homo Sapiens

<400> SEQUENCE: 116
gaaaguacag aucggauggg u                                               21
```

```
<210> SEQ ID NO 117
<211> LENGTH: 22
<212> TYPE: RNA
<213> ORGANISM: Homo Sapiens

<400> SEQUENCE: 117
uaugugccuu uggacuacau cg                                               22

<210> SEQ ID NO 118
<211> LENGTH: 21
<212> TYPE: RNA
<213> ORGANISM: Homo Sapiens

<400> SEQUENCE: 118
cuacaggcug gaaugggcuc a                                                21

<210> SEQ ID NO 119
<211> LENGTH: 21
<212> TYPE: RNA
<213> ORGANISM: Homo Sapiens

<400> SEQUENCE: 119
ucuaguaaga guggcagucg a                                                21

<210> SEQ ID NO 120
<211> LENGTH: 22
<212> TYPE: RNA
<213> ORGANISM: Homo Sapiens

<400> SEQUENCE: 120
gaugagcuca uuguaauaug ag                                               22

<210> SEQ ID NO 121
<211> LENGTH: 21
<212> TYPE: RNA
<213> ORGANISM: Homo Sapiens

<400> SEQUENCE: 121
cgggagcugg ggucugcagg u                                                21

<210> SEQ ID NO 122
<211> LENGTH: 21
<212> TYPE: RNA
<213> ORGANISM: Homo Sapiens

<400> SEQUENCE: 122
aagcauucuu ucauugguug g                                                21

<210> SEQ ID NO 123
<211> LENGTH: 18
<212> TYPE: RNA
<213> ORGANISM: Homo Sapiens

<400> SEQUENCE: 123
cggggcggca ggggccuc                                                    18

<210> SEQ ID NO 124
<211> LENGTH: 22
<212> TYPE: RNA
<213> ORGANISM: Homo Sapiens

<400> SEQUENCE: 124
gugaggaggg gcuggcaggg ac                                               22
```

<210> SEQ ID NO 125
<211> LENGTH: 22
<212> TYPE: RNA
<213> ORGANISM: Homo Sapiens

<400> SEQUENCE: 125
agugggagga caggaggcag gu                                          22

<210> SEQ ID NO 126
<211> LENGTH: 22
<212> TYPE: RNA
<213> ORGANISM: Homo Sapiens

<400> SEQUENCE: 126
ccaggaggcg gaggaggugg ag                                          22

<210> SEQ ID NO 127
<211> LENGTH: 22
<212> TYPE: RNA
<213> ORGANISM: Homo Sapiens

<400> SEQUENCE: 127
ugguugacca uagaacaugc gc                                          22

<210> SEQ ID NO 128
<211> LENGTH: 22
<212> TYPE: RNA
<213> ORGANISM: Homo Sapiens

<400> SEQUENCE: 128
uugcuugaac ccaggaagug ga                                          22

<210> SEQ ID NO 129
<211> LENGTH: 22
<212> TYPE: RNA
<213> ORGANISM: Homo Sapiens

<400> SEQUENCE: 129
cuauacaacc uacugccuuc cc                                          22

<210> SEQ ID NO 130
<211> LENGTH: 17
<212> TYPE: RNA
<213> ORGANISM: Homo Sapiens

<400> SEQUENCE: 130
ggagugggcu ggugguu                                                17

<210> SEQ ID NO 131
<211> LENGTH: 21
<212> TYPE: RNA
<213> ORGANISM: Homo Sapiens

<400> SEQUENCE: 131
cggcggggac ggcgauuggu c                                           21

<210> SEQ ID NO 132
<211> LENGTH: 21
<212> TYPE: RNA
<213> ORGANISM: Homo Sapiens

<400> SEQUENCE: 132

```
agggagggac gggggcugug c                                         21

<210> SEQ ID NO 133
<211> LENGTH: 22
<212> TYPE: RNA
<213> ORGANISM: Homo Sapiens

<400> SEQUENCE: 133
aaaggaaagu guauccuaaa ag                                        22

<210> SEQ ID NO 134
<211> LENGTH: 22
<212> TYPE: RNA
<213> ORGANISM: Homo Sapiens

<400> SEQUENCE: 134
cguguucaca gcggaccuug au                                        22

<210> SEQ ID NO 135
<211> LENGTH: 20
<212> TYPE: DNA
<213> ORGANISM: Artificial sequence
<220> FEATURE:
<223> OTHER INFORMATION: Probe

<400> SEQUENCE: 135
atcgctttac cattcatgtt                                           20

<210> SEQ ID NO 136
<211> LENGTH: 24
<212> TYPE: DNA
<213> ORGANISM: Artificial sequence
<220> FEATURE:
<223> OTHER INFORMATION: Probe

<400> SEQUENCE: 136
gttccacact gacactgcag aagt                                      24

<210> SEQ ID NO 137
<211> LENGTH: 21
<212> TYPE: DNA
<213> ORGANISM: Artificial sequence
<220> FEATURE:
<223> OTHER INFORMATION: Probe

<400> SEQUENCE: 137
caggagtggg gggtgggacg t                                         21

<210> SEQ ID NO 138
<211> LENGTH: 21
<212> TYPE: DNA
<213> ORGANISM: Artificial sequence
<220> FEATURE:
<223> OTHER INFORMATION: Probe

<400> SEQUENCE: 138
acacttgttg ggatgacctg c                                         21

<210> SEQ ID NO 139
<211> LENGTH: 22
<212> TYPE: DNA
<213> ORGANISM: Artificial sequence
<220> FEATURE:
<223> OTHER INFORMATION: Probe

<400> SEQUENCE: 139
```

```
agattgtttc ttttgccgtg ca                                          22

<210> SEQ ID NO 140
<211> LENGTH: 22
<212> TYPE: DNA
<213> ORGANISM: Artificial sequence
<220> FEATURE:
<223> OTHER INFORMATION: Probe

<400> SEQUENCE: 140
tgaggggttt ggaatgggat gg                                          22

<210> SEQ ID NO 141
<211> LENGTH: 18
<212> TYPE: DNA
<213> ORGANISM: Artificial sequence
<220> FEATURE:
<223> OTHER INFORMATION: Probe

<400> SEQUENCE: 141
aggctgggct gggacgga                                               18

<210> SEQ ID NO 142
<211> LENGTH: 18
<212> TYPE: DNA
<213> ORGANISM: Artificial sequence
<220> FEATURE:
<223> OTHER INFORMATION: Probe

<400> SEQUENCE: 142
aggctggagt gagcggag                                               18

<210> SEQ ID NO 143
<211> LENGTH: 22
<212> TYPE: DNA
<213> ORGANISM: Artificial sequence
<220> FEATURE:
<223> OTHER INFORMATION: Probe

<400> SEQUENCE: 143
cacttagcag gttgtattat at                                          22

<210> SEQ ID NO 144
<211> LENGTH: 20
<212> TYPE: DNA
<213> ORGANISM: Artificial sequence
<220> FEATURE:
<223> OTHER INFORMATION: Probe

<400> SEQUENCE: 144
aaatgggtgg tctgaggcaa                                             20

<210> SEQ ID NO 145
<211> LENGTH: 17
<212> TYPE: DNA
<213> ORGANISM: Artificial sequence
<220> FEATURE:
<223> OTHER INFORMATION: Probe

<400> SEQUENCE: 145
accccactcc tggtacc                                                17

<210> SEQ ID NO 146
<211> LENGTH: 21
<212> TYPE: DNA
```

```
<213> ORGANISM: Artificial sequence
<220> FEATURE:
<223> OTHER INFORMATION: Probe

<400> SEQUENCE: 146
tggggcgggg caggtccctg c                                              21

<210> SEQ ID NO 147
<211> LENGTH: 22
<212> TYPE: DNA
<213> ORGANISM: Artificial sequence
<220> FEATURE:
<223> OTHER INFORMATION: Probe

<400> SEQUENCE: 147
tttgtgacct ggtccactaa cc                                             22

<210> SEQ ID NO 148
<211> LENGTH: 17
<212> TYPE: DNA
<213> ORGANISM: Artificial sequence
<220> FEATURE:
<223> OTHER INFORMATION: Probe

<400> SEQUENCE: 148
gtggacctgg ctgggac                                                   17

<210> SEQ ID NO 149
<211> LENGTH: 22
<212> TYPE: DNA
<213> ORGANISM: Artificial sequence
<220> FEATURE:
<223> OTHER INFORMATION: Probe

<400> SEQUENCE: 149
caacctggag gactccatgc tg                                             22

<210> SEQ ID NO 150
<211> LENGTH: 25
<212> TYPE: DNA
<213> ORGANISM: Artificial sequence
<220> FEATURE:
<223> OTHER INFORMATION: Probe

<400> SEQUENCE: 150
gtgaggcggg gccaggaggg tgtgt                                          25

<210> SEQ ID NO 151
<211> LENGTH: 23
<212> TYPE: DNA
<213> ORGANISM: Artificial sequence
<220> FEATURE:
<223> OTHER INFORMATION: Probe

<400> SEQUENCE: 151
ggaggcgcag gctcggaaag gcg                                            23

<210> SEQ ID NO 152
<211> LENGTH: 22
<212> TYPE: DNA
<213> ORGANISM: Artificial sequence
<220> FEATURE:
<223> OTHER INFORMATION: Probe

<400> SEQUENCE: 152
agtgcctgct atgtgccagg ca                                             22
```

<210> SEQ ID NO 153
<211> LENGTH: 23
<212> TYPE: DNA
<213> ORGANISM: Artificial sequence
<220> FEATURE:
<223> OTHER INFORMATION: Probe

<400> SEQUENCE: 153
aggttgggat cggttgcaat gct                                              23

<210> SEQ ID NO 154
<211> LENGTH: 21
<212> TYPE: DNA
<213> ORGANISM: Artificial sequence
<220> FEATURE:
<223> OTHER INFORMATION: Probe

<400> SEQUENCE: 154
gaaagtacag atcggatggg t                                                21

<210> SEQ ID NO 155
<211> LENGTH: 22
<212> TYPE: DNA
<213> ORGANISM: Artificial sequence
<220> FEATURE:
<223> OTHER INFORMATION: Probe

<400> SEQUENCE: 155
tatgtgcctt tggactacat cg                                               22

<210> SEQ ID NO 156
<211> LENGTH: 21
<212> TYPE: DNA
<213> ORGANISM: Artificial sequence
<220> FEATURE:
<223> OTHER INFORMATION: Probe

<400> SEQUENCE: 156
ctacaggctg gaatgggctc a                                                21

<210> SEQ ID NO 157
<211> LENGTH: 21
<212> TYPE: DNA
<213> ORGANISM: Artificial sequence
<220> FEATURE:
<223> OTHER INFORMATION: Probe

<400> SEQUENCE: 157
tctagtaaga gtggcagtcg a                                                21

<210> SEQ ID NO 158
<211> LENGTH: 22
<212> TYPE: DNA
<213> ORGANISM: Artificial sequence
<220> FEATURE:
<223> OTHER INFORMATION: Probe

<400> SEQUENCE: 158
gatgagctca ttgtaatatg ag                                               22

<210> SEQ ID NO 159
<211> LENGTH: 21
<212> TYPE: DNA
<213> ORGANISM: Artificial sequence
<220> FEATURE:

<223> OTHER INFORMATION: Probe

<400> SEQUENCE: 159
cgggagctgg ggtctgcagg t                                          21

<210> SEQ ID NO 160
<211> LENGTH: 21
<212> TYPE: DNA
<213> ORGANISM: Artificial sequence
<220> FEATURE:
<223> OTHER INFORMATION: Probe

<400> SEQUENCE: 160
aagcattctt tcattggttg g                                          21

<210> SEQ ID NO 161
<211> LENGTH: 18
<212> TYPE: DNA
<213> ORGANISM: Artificial sequence
<220> FEATURE:
<223> OTHER INFORMATION: Probe

<400> SEQUENCE: 161
cggggcggca ggggcctc                                              18

<210> SEQ ID NO 162
<211> LENGTH: 22
<212> TYPE: DNA
<213> ORGANISM: Artificial sequence
<220> FEATURE:
<223> OTHER INFORMATION: Probe

<400> SEQUENCE: 162
gtgaggaggg gctggcaggg ac                                         22

<210> SEQ ID NO 163
<211> LENGTH: 22
<212> TYPE: DNA
<213> ORGANISM: Artificial sequence
<220> FEATURE:
<223> OTHER INFORMATION: Probe

<400> SEQUENCE: 163
agtgggagga caggaggcag gt                                         22

<210> SEQ ID NO 164
<211> LENGTH: 22
<212> TYPE: DNA
<213> ORGANISM: Artificial sequence
<220> FEATURE:
<223> OTHER INFORMATION: Probe

<400> SEQUENCE: 164
ccaggaggcg gaggaggtgg ag                                         22

<210> SEQ ID NO 165
<211> LENGTH: 22
<212> TYPE: DNA
<213> ORGANISM: Artificial sequence
<220> FEATURE:
<223> OTHER INFORMATION: Probe

<400> SEQUENCE: 165
tggttgacca tagaacatgc gc                                         22

-continued

```
<210> SEQ ID NO 166
<211> LENGTH: 22
<212> TYPE: DNA
<213> ORGANISM: Artificial sequence
<220> FEATURE:
<223> OTHER INFORMATION: Probe

<400> SEQUENCE: 166
ttgcttgaac ccaggaagtg ga                                              22

<210> SEQ ID NO 167
<211> LENGTH: 22
<212> TYPE: DNA
<213> ORGANISM: Artificial sequence
<220> FEATURE:
<223> OTHER INFORMATION: Probe

<400> SEQUENCE: 167
ctatacaacc tactgccttc cc                                              22

<210> SEQ ID NO 168
<211> LENGTH: 17
<212> TYPE: DNA
<213> ORGANISM: Artificial sequence
<220> FEATURE:
<223> OTHER INFORMATION: Probe

<400> SEQUENCE: 168
ggagtgggct ggtggtt                                                    17

<210> SEQ ID NO 169
<211> LENGTH: 21
<212> TYPE: DNA
<213> ORGANISM: Artificial sequence
<220> FEATURE:
<223> OTHER INFORMATION: Probe

<400> SEQUENCE: 169
cggcggggac ggcgattggt c                                               21

<210> SEQ ID NO 170
<211> LENGTH: 21
<212> TYPE: DNA
<213> ORGANISM: Artificial sequence
<220> FEATURE:
<223> OTHER INFORMATION: Probe

<400> SEQUENCE: 170
agggagggac ggggctgtg c                                                21

<210> SEQ ID NO 171
<211> LENGTH: 22
<212> TYPE: DNA
<213> ORGANISM: Artificial sequence
<220> FEATURE:
<223> OTHER INFORMATION: Probe

<400> SEQUENCE: 171
aaaggaaagt gtatcctaaa ag                                              22
```

```
<210> SEQ ID NO 172
<211> LENGTH: 22
<212> TYPE: DNA
<213> ORGANISM: Artificial sequence
<220> FEATURE:
<223> OTHER INFORMATION: Probe

<400> SEQUENCE: 172
cgtgttcaca gcggaccttg at                                              22
```